United States Patent [19]
Freimer et al.

[11] Patent Number: 6,136,532
[45] Date of Patent: Oct. 24, 2000

[54] METHODS FOR TREATING BIPOLAR MOOD DISORDER ASSOCIATED WITH MARKERS ON CHROMOSOME 18Q

[75] Inventors: Nelson B. Freimer, San Francisco, Calif.; Lodewijk Sandkuijl, Delft, Netherlands; Pedro Leon, San Jose, Costa Rica; Victor I. Reus, San Francisco, Calif.; Michael Escamilla, San Francisco, Calif.; Lynne Allison McInnes, San Francisco, Calif.

[73] Assignees: The Regents of the University of California, Oakland, Calif.; The University of Costa Rica, San Jose, Costa Rica

[21] Appl. No.: 08/976,752

[22] Filed: Nov. 24, 1997

Related U.S. Application Data

[63] Continuation of application No. 08/824,976, Mar. 27, 1997, abandoned.
[60] Provisional application No. 60/014,498, Mar. 29, 1996, and provisional application No. 60/023,438, Aug. 23, 1996.
[51] Int. Cl.[7] .............................. C12Q 1/68; C12P 19/34; C07H 21/02; C07H 21/04
[52] U.S. Cl. ........................... 435/6; 435/91.2; 536/23.1; 536/23.5
[58] Field of Search ..................... 435/6, 91.2; 536/23.1, 536/23.5

[56] References Cited

PUBLICATIONS

Stine et al. Am. J. Hum. Genet. 57:1384–1394, 1995.
Baron. Molecular Psychiatry. 2:200–210, 1997.
Craddock et al. J. of Medical Genet. 36(8):585–594, 1999.
Berrettini et al. Annals Of Medicine,28 (3) 191–4, Jun. 1996.
Baron et al., "Genetic linkage between X–chomosomes markers and bipolar affective illness" Nature, vol. 326:289–292 (1987).
Baron et al., "Diminished support for linkage between manic depressive illness and X–chromosome markers in three Israeli pedigrees", Nature Genetics, vol. 3:49–55 (1993).
Berrettinni et al., "Chromosome 18 DNA markers and manic–depressive illness: Evidence for a susceptibility gene", Proc. .Natl. Acad. Sci. USA, vol. 91:5918–5921 (1994).
Bertelsen et al.,"A Danish Twin Study of Manic–Depressive Disorders", Brit. J. Psychiat. vol. 130:330–351 (1977).
Boehnke, "Allele Frequency Estimation from Data on Relatives", Amer. J. Hum. Genet., vol. 48:22–25 (1991).
Cohen et al., "A first–generation physical map of the human genome" Nature, vol. 366:698–701 (1993).
Copeman et al., "Linkage disequilibrium mapping of a type 1 diabetes susceptibilty gene(IDDM7) to chromosome 2q31–q33" Nature Genet., vol.9:80–85 (1995).
Dausset, et al., "Centre d"Etude du Polymorphisme Humain (CEPH): Collaborative Genetic Mapping of the Human Genome" Genomics, vol. 6:575–577 (1990).
Davies, et al., "A genome–wide search for human type 1 diabetes susceptibility genes", Nature, vol. 371:130–136 (1994).
Detera–Wadleigh, et al., "Genetic Linkage Mapping for a Susceptibility Locus to Bipolar Illnesss: Chromosomes 2,3, 4,7,9,10p, 11p, 22, and Xpter" Amer. J. of Med. Gene. (Neuropsychiatric Genetics), vol. 54:206–218, (1994).
Di Bella, et al., "Association study of a null mutation in the dopamine D4 receptor gene in Italian patients with obses-sive–compulsive disorder, bipolar mood disorder and schizophrenia", Psychiatric Genetics, vol. 6:119–121, (1996).
Di Rienzo, et al., "Mutational processes of simple–sequence repeat loci in human populations", Proc. Natl. Acad. Sci. USA, vol. 91:3166–3170, (1994).
Edwards, "The analysis of X–linkage", Ann. Hum. Genet., Lond., vol. 34:229–250, (1971).
Egeland, et al., "Bipolar affective disorders linked to DNA markers on chromosome 11", Nature, vol. 325:783–787, (1987).
Endicott, et al., A Diagnostic Interview, Arch. Gen. Psychia-try, vol. 35:837–844, (1978).
Escamilla, et al., "Use of Linkage Disequilibrium Approaches to Map Genes for Bipolar Disorder in the Costa Rican Population", Amer. J. of Med. Gene. (Neuropsychiat-ric Genetics), vol. 67:244–253, (1996).
Freimer, et al., "the Genetics of Bipolar Disorder & Schizo-phrenia", Bipolar Disorder and Schizophrenia Ch. 64:951–965, (1992).
Freimer, et al., The molecular and genetic basis of neuro-logical disease, 951–965, (1993).
Freimer, et al., "Microsatellites: evolution and mutational processes", Microsatellites Freimer & Slatkin, pp. 51–72, undated.

(List continued on next page.)

Primary Examiner—Jeffrey Fredman
Assistant Examiner—Juliet C. Einsmann
Attorney, Agent, or Firm—Carol L. Francis; Paula A. Borden; Bozicevic, Field & Francis LLP

[57] ABSTRACT

The present invention is directed to methods of detecting the presence of a bipolar mood disorder susceptibility locus in an individual, comprising analyzing a sample of DNA for the presence of a DNA polymorphism on the long arm of chromosome 18 between markers D18S469 and D18S554, wherein the DNA polymorphism is associated with a form of bipolar mood disorder. The invention for the first time provides strong evidence of a susceptibility gene for bipolar mood disorder that is located in the 18q22-q23 region of the long arm of chromosome 18. The disclosure describes the use of linkage analysis and genetic markers in this 18q22-q23 region to fine map the region and the use of genetic markers to genetically diagnose (genotype) bipolar mood disorder in individuals, to confirm phenotypic diagnoses of bipolar mood disorder, to determine appropriate treatments for patients with particular genotypic subtypes. Isolated polynucleotides useful for genetic linkage analysis of BP-I and methods for obtaining such isolated polynucleotides are also described.

18 Claims, 11 Drawing Sheets

PUBLICATIONS

Freimer, et al., "An Approach to Investigation Linkage for Bipolar Disorder Using Large Costa Rican Pedigrees", *Amer. J. of Med. Gene. (Neuropsychiatric Genetics)*, vol.67:254–263 (1996).

Freimer, et al., "Genetic mapping using haplotype, association and linkage methods suggests a locus for severe bipolar disorder (BPI) at 18q22–q23", *Nature Genet.*, vol. 12:436–441, (1996).

Garza, et al., "Microsatellite allele frequencies in humans and chimpanzees, with implications for constraints on allele size", *Mol. Biol. Evol.*, vol. 12:594–603 (1995).

van Kessel, et al., "Report of the second international workshop on human chromosome 18 mapping", Cytogenet. Cell Genet., vol. 65:142–158 (1994).

Gerson, "Genetics", *Manic Depressive Illness*, Goodwin, et al. Ch. 15 pp.373–401, Goodwin, F.K., et al., (1990).

Gyapay, et al., "The 1993–94 Genethon human genetic linkage map", *Nature Genet.*, vol. 7:246–339 (1994).

Hastabacka, et al., "The Diastrophic Dysplasia Gene Encodes a Novel Sulfate Transporter: Positional Cloning by Fine–Structure Linkage Disequilibrium Mapping", *Cell*, vol. 78:10073–1087, (1994).

Hudson, et al., "Isolation and Chromosomal Assignment of 100 Highly Informative Human Simple Sequence Repeat Polymorphisms", *Genomics*, vol. 13: 622–629, (1992).

Kelsoe, "Re–evaluation of the linkage relationship between chromosome 11p loci and the gene for bipolar affective disorder in the Old Order Amish" *Nature*, vol. 342:238–243 (1989).

Kerem, et al., "Identification of the Cystic Fibrosis Gene: Genetic Analysis", *Science*, vol. 245:1073–1080 (1989).

Lander, et al., "Mapping Complex Genetic Traits in Humans: New Methods Using a Complete RFLP Linkage Map", *Cold Spring Harbor Symposium on Quantitative Biology*, vol. LI pp. 49–62 (1986).

Lander, et al., "Genetic Dissection of Complex Traits", *Science*, vol. 265:2037–2048. (1994).

Lathrop, et al., "Statagies for multilocus linkage analysis in humans." *Proc. Natl. Sci. USA*, vol. 81:3443–3446, (1984).

Le Beau, et al., "Report of the First International Workshop on Human Chromosome 18 Mapping 1992", *Cytogenet. Cell Genet.*, vol. 63:77–95 (1993).

Leon, et al., "The gene for an inherited form of deafness maps to chromosome 5q31", *Proc. Natl. Acad. Sci. USA*, vol. 89:5181–5184 (1992).

Lovett, et al., "Direct selection: A method for the isolation of cDNAs encoded by large genomic regions", *Proc. Natl. Acad. Sci. USA*, vol. 88:9628–9632 (1991).

Maier, et al., "Linkage analysis between pericentrometric markers on chromosome 18 and bipolar disorder: A replication test", *Psych. Res.*, vol. 59:7–15 (1995).

McInnes, et al., "Mapping genes for psychiatric disorders and behavioral traits", *Current Opinions in Genetic and Developments*, vol. 5:376–381 (1995).

McInnes, et al., "A complete genome screen for genes predisposing to severe bipolar disorder in two Costa Rican pedigrees", *Proc. Natl. Acad. Sci. USA*, vol. 93:13060–13065 (1996).

Murray, et al., "A Comprehensive Human Linkage Map with Centimorgen Density", *Science*, vol. 265:2049–2054 (1994).

Nurnberger, et al., "Diagnostic Interview for Genetic Studies", *Arch. Gen. Psychiatry*, vol. 51:849–859 (1994).

Nystrom–Lahti, et al., "Close linkage to chromosome 3p and conservation of ancestral founding haplotype in hereditary nonpolyposis colorectal cancer families", *Proc. Natl. Acad. Sci. USA*, vol. 91:6054–6058 (1994).

Ott, *Analysis of Human Genetic Linkage*, 2nd Ed., John Hopkins University Press, Baltimore (1991).

Pauls, et al., "Linkage Analysis of Chromosome 18 Markers Do Not Identify a Major Susceptibility Locus for Bipolar Affective Disorder in the Old Order Amish", *Amer. J. Hum. Genet.*, vol. 57:636–643 (1995).

Petrukhin, et al., "A Microsatellite Genetic Linkage Map of Human Chromosome 13", *Genomics* vol. 15:76–85 (1993).

Puffenberger, et al., "A Missense Mutation of the Endothelin–B Receptor Gene in Multigenic Hirschsprung's Disease", *Cell*, Vol. 79:1257–1266 (1994).

Puffenberger, et al., "Identify–by–descent and association mapping of a recessive gene for Hirschsprung disease on human chromosome 13q22", *Human Mol. Genet.*, vol.3, No. 8 pp. 1217–1225 (1994).

Spielman, et al., "Transmission Test for Linkage Disequilibrium: The Insulin Gene Region and Insulin–dependent Diabetes Mellitus (IDDM)", *Amer. J. Hum. Genet.*, vol. 52:506–516 (1993).

Straub, et al., "A possible vulnerability locus for bipolar affective disorder on chromosome 21q22.3", *Nature Genetics*, vol. 8:291–296 (1994).

Terwilliger, "A Powerful Likelihood Method for the Analysis of Linkage Disequilibrium between Trait Loci and One or More Polymorphic Marker Loci", *Amer. J. Hum. Genet.*, vol. 56:777–787 (1995).

Weber. "Informativeness of Human $(dC–dA)_n$ $(dG–dT)_n$ Polymorphisms" *Genomics*, vol. 7:524–530 (1990).

Weissenbach, et al., "A second–generation linkage map of the human genome", *Nature*, vol. 359:794–801 (1992).

Yoshikawa, et al., "Isolation of Chromosome 18–Specific Brain Transcripts as Positional Candidates for Bipolar Disorder", *Amer. J. of Med. Gene. (Neuropsychiatric Genetics)*, vol. 74:140–149 (1997).

Uhrhammer, et al., "Sublocalization of an Ataxia–Telangiectasia Gene Distal to D11S384 by Ancestral Haplotyping in Costa Rican Families", *Amer. J. Hum. Genet.*, vol. 57:103–111 (1995).

FIG.2

| Marker name | Distance from pter, cM | Family CR001 | | Family CR004 | | Combined | |
|---|---|---|---|---|---|---|---|
| | | $Z_{max} \geq 0.8$ | $\theta$ | $Z_{max} \geq 1.2$ | $\theta$ | $Z_{med} \geq 1.6$ | $\theta$ |
| D1S456 | 224.6 | 1.32 | 0.0 | 0.0 | 0.50 | 0.0 | 0.50 |
| D2S130 | 230.1 | 0.89 | 0.0 | 0.12 | 0.35 | 0.36 | 0.26 |
| D3S1285 | 91.0 | 0.00 | 0.50 | 2.59 | 0.00 | 1.15 | 0.16 |
| D4S171 | 207.9 | 1.07 | 0.07 | 0.01 | 0.05 | 0.22 | 0.29 |
| D5S427 | 69.6 | 1.39 | 0.0 | 0.0 | 0.50 | 0.7 | 0.18 |
| D7S510 | 60.5 | 0.04 | 0.40 | 2.04 | 0.0 | 0.82 | 0.17 |
| D11S929 | 36.3 | 0.80 | 0.11 | 0.03 | 0.42 | 0.43 | 0.24 |
| D11S1392 | 38.6 | 0.86 | 0.07 | 0.90 | 0.23 | 1.58 | 0.19 |
| D11S1312 | 42.0 | 0.47 | 0.13 | 1.77 | 0.0 | 1.95 | 0.05 |
| D13S175 | 7.4 | 0.83 | 0.0 | 0.0 | 0.50 | 0.24 | 0.15 |
| D15S126 | 45.5 | 1.09 | 0.0 | 0.0 | 0.48 | 0.06 | 0.40 |
| D16S521 | 4.6 | 1.46 | 0.0 | 0.41 | 0.26 | 1.18 | 0.17 |
| D16S515 | 94.8 | 0.93 | 0.09 | 0.01 | 0.46 | 0.39 | 0.25 |
| D16S486 | 133.6 | 0.27 | 0.19 | 1.29 | 0.20 | 1.60 | 0.20 |
| D17S849 | 0.60 | 0.0 | 0.50 | 1.22 | 0.07 | 0.32 | 0.14 |
| D18S59 | 1.1 | 1.43 | 0.0 | 0.0 | 0.50 | 0.02 | 0.46 |
| D18S1105 | 2.8 | 0.97 | 0.0 | 0.01 | 0.47 | 0.01 | 0.46 |
| D18S71 | 43.8 | 0.96 | 0.0 | 0.0 | 0.50 | 0.0 | 0.50 |
| D18S64 | 84.0 | 0.33 | 0.11 | 1.34 | 0.15 | 1.67 | 0.13 |
| D18S55 | 95.5 | 0.0 | 0.50 | 2.09 | 0.13 | 1.51 | 0.18 |
| D18S61 | 103.8 | 0.0 | 0.50 | 2.26 | 0.12 | 1.94 | 0.16 |
| D18S488 | 105.6 | 0.0 | 0.50 | 1.26 | 0.14 | 1.02 | 0.19 |
| D18S1161 | 113.0 | 0.0 | 0.50 | 1.79 | 0.16 | 1.76 | 0.17 |

FIG. 5A

| Distance from pter (in cM) | 84 | 95.5 | 104 | 106 | 108 | 110 | 113 | 115 | 115 | 116 | 118 | 119 | 119 | 125 |
|---|---|---|---|---|---|---|---|---|---|---|---|---|---|---|
| Marker | 64 | 55 | 61 | 485 | 870 | 469 | 1161 | 1121 | 1009 | 380 | 554 | 462 | 461 | 70 |
| V-17 | 188 | 138 | 175 | 176 | 179 | 236 | 106 | 173 | 162 | 154 | 218 | 193 | 166 | 124 |
| V-16 | 188 | 138 | 175 | 176 | 179 | 236 | 106 | 168 | 150 | 150 | 218 | 193 | 166 | 124 |
| V-8 | 188 | 138 | 175 | 176 | 179 | 236 | 106 | 168 | 150 | 150 | 222 | 187 | 168 | 124 |
| IV-24 | 188 | 138 | 175 | 176 | 179 | 236 | 106 | 168 | 150 | 150 | 222 | 187 | 168 | 124 |
| IV-30 | 188 | 138 | 175 | 176 | 179 | 236 | 106 | 168 | 150 | 150 | 222 | 187 | 168 | 124 |
| V-6 # | 188 | 138 | 175 | 176 | 179 | 236 | 106 | 168 | 150 | 150 | 222 | 187 | 168 | 124 |
| V-15 | 188 | 138 | 175 | 176 | 179 | 236 | 106 | 168 | 150 | 150 | 222 | 187 | 168 | 124 |
| V-19 | 188 | 138 | 175 | 176 | 179 | 236 | 106 | 168 | 150 | 150 | 222 | 187 | 168 | 124 |
| V-9 * | 188 | 146 | 175 | 176 | 179 | 236 | 106 | 168 | 150 | 150 | 222 | 187 | 168 | 124 |
| V-13 | 188 | 146 | 175 | 176 | 179 | 236 | 106 | 168 | 150 | 150 | 222 | 187 | 168 | 124 |
| V-14 | 188 | 146 | 175 | 176 | 179 | 236 | 106 | 168 | 150 | 150 | 222 | 187 | 168 | 124 |
| IV-17 # | 188 | 142 | 159 | 182 | 179 | 242 | 106 | 168 | 150 | 150 | 222 | 187 | 168 | 124 |
| IV-18 @ | 188 | 142 | 159 | 182 | 179 | 242 | 106 | 168 | 150 | 150 | 222 | 187 | 168 | 124 |
| V-11 | 188 | 142 | 159 | 182 | 179 | 242 | 106 | 168 | 150 | 150 | 222 | 187 | 168 | 124 |
| VI-2 | 192 | 138 | 157 | 188 | 179 | 242 | 106 | 168 | 150 | 150 | 222 | 187 | 168 | 124 |
| VI-1 # | 200 | 142 | 173 | 182 | 179 | 236 | 106 | 168 | 150 | 150 | 222 | 187 | 167 | 122 |
| VI-1 # | 188 | 138 | 177 | 186 | 179 | 236 | 96 | 168 | 150 | 150 | 216 | 185 | 164 | 124 |
| V-7 # | 188 | 138 | 177 | 186 | 179 | 236 | 96 | 168 | 150 | 150 | 216 | 185 | 164 | 114 |
| V-2 * | 192 | 140 | 159 | 178 | 171 | 236 | 94 | 166 | 150 | 150 | 222 | 183 | 163 | 110 |
| IV-6 | 192 | 140 | 159 | 178 | 171 | 236 | 94 | 166 | 150 | 150 | 222 | 183 | 163 | 110 |
| IV-9 @ | 192 | 140 | 159 | 178 | 171 | 236 | 94 | 166 | 150 | 150 | 222 | 183 | 163 | 110 |
| V-3 | 192 | 140 | 159 | 178 | 171 | 236 | 94 | 166 | 150 | 150 | 222 | 183 | 163 | 110 |
| V-6 # | 192 | 140 | 159 | 186 | 171 | 236 | 94 | 166 | 150 | 150 | 222 | 183 | 163 | 110 |
| V-7 # | 192 | 142 | 159 | 182 | 171 | 236 | 100 | 173 | 150 | 150 | 222 | 183 | 164 | 122 |
| V-10 | 192 | 142 | 171 | 182 | 171 | 236 | 100 | 173 | 150 | 150 | 222 | 183 | 164 | 122 |
| IV-19 | 204 | 144 | 171 | 182 | 171 | 236 | 100 | 173 | 150 | 150 | 222 | 183 | 164 | 122 |
| IV-17 # | 202 | 146 | 179 | 182 | 171 | 236 | 100 | 173 | 150 | 150 | 222 | 183 | 164 | 122 |

FIG. 5B

| Distance from pter (in cM) | 84 | 95.5 | 104 | 106 | 108 | 110 | 113 | 115 | 115 | 116 | 118 | 119 | 119 | 125 |
|---|---|---|---|---|---|---|---|---|---|---|---|---|---|---|
| Marker | 64 | 55 | 61 | 485 | 870 | 469 | 1161 | 1121 | 1009 | 380 | 554 | 462 | 461 | 70 |
| IV-6 | 188 | 146 | 173 | 178 | 175 | 236 | 96 | 175 | 150 | 148 | 216 | 189 | 164 | 112 |
| IV-9 | 188 | 146 | 173 | 186 | 179 | 236 | 94 | 166 | 146 | 145 | 218 | 183 | 164 | 114 |
| IV-18 | 204 | 144 | 171 | 182 | 179 | 236 | 108 | 166 | 154 | 146 | 216 | 187 | 164 | 111 |
| IV-19 | 192 | 142 | 159 | 186 | 179 | 236 | 96 | 164 | 150 | 155 | 218 | 185 | 164 | 118 |
| IV-24 | 190 | 140 | 177 | 186 | 179 | 236 | 90 | 173 | 162 | 154 | 218 | 193 | 166 | 124 |
| IV-30 | 190 | 144 | 175 | 178 | 175 | 236 | 90 | 175 | 150 | 155 | 218 | 185 | 164 | 112 |
| V-3 | 200 | 144 | 169 | 182 | 187 | 242 | 96 | 168 | 154 | 150 | 218 | 183 | 169 | 106 |
| V-8 | 192 | 142 | 171 | 182 | 179 | 236 | 102 | 166 | 150 | 154 | 216 | 187 | 164 | 128 |
| V-10 | 192 | 142 | 179 | 186 | 179 | 236 | 96 | 168 | 156 | 145 | 216 | 183 | 167 | 118 |
| V-11 | 192 | 138 | 179 | 180 | 175 | 242 | 104 | 166 | 158 | 150 | 216 | 183 | 162 | 118 |
| V-13 | 192 | 146 | 171 | 182 | 179 | 238 | 90 | 175 | 150 | 150 | 216 | 183 | 167 | 124 |
| V-14 | 192 | 138 | 173 | 182 | 179 | 236 | 94 | 164 | 152 | 150 | 222 | 185 | 167 | 124 |
| V-19 | 190 | 150 | 177 | 182 | 179 | 236 | 104 | 168 | 150 | 155 | 218 | 191 | 167 | 124 |
| V-15,16,17 | 192 | 138 | 157 | 188 | 179 | 242 | 104 | 168 | 148 | 145 | 222 | 185 | 160 | 114 |
|  | 206 | 144 | 173 | 186 | 179 | 236 | 94 | 166 | 146 | 145 | 218 | 183 | 164 | 114 |
|  | 200 | 144 | 159 | 186 | NT | 242 | NT | 166 | 148 | 150 | 216 | 193 | 164 | 124 |
|  | 192 | 142 | 171 | 182 | 179 | 236 | 90 | 175 | 150 | 150 | 216 | 183 | 164 | 111 |
|  | 190 | 140 | 177 | 186 | 179 | 236 | 90 | 173 | 150 | 154 | 216 | 185 | 164 | 118 |
|  | 188 | 138 | 179 | 182 | 183 | 240 | 96 | 168 | 150 | 150 | 218 | 187 | 164 | 120 |
|  | 188 | 146 | 159 | 186 | 179 | 236 | 96 | 164 | 150 | 154 | 216 | 185 | 164 | 128 |
|  | 188 | 142 | 157 | 178 | 175 | 236 | 98 | 181 | 148 | 150 | 218 | 185 | 163 | 112 |
|  | 188 | 148 | 177 | 182 | 179 | 236 | 96 | 166 | 150 | 145 | 226 | 183 | 167 | 114 |

METHODS FOR TREATING BIPOLAR MOOD DISORDER ASSOCIATED WITH MARKERS ON CHROMOSOME 18Q

CROSS-REFERENCE TO RELATED APPLICATIONS

This application is a continuation application of U.S. application Ser. No. 08/824,976 filed Mar. 27, 1997 now abandoned and claims the benefit of the filing dates of U.S. Provisional Application Ser. No. 60/014,498, filed Mar. 29, 1996 and U.S. Ser. No. 60/023,438, filed Aug. 23, 1996.

ACKNOWLEDGEMENTS

This invention was made with Government support under Grant Nos. RO1-MH49499, K21MH00916, MH48695, and MH47563, awarded by the NIH. The U.S. Government has certain rights in this invention.

INTRODUCTION

Background

BIPOLAR MOOD DISORDER (BP)

Manic-depressive illness, or bipolar mood disorder (BP), is characterized by episodes of elevated mood (mania) and depression and is among the most prevalent and potentially devastating of psychiatric syndromes. The most severe and clinically distinctive forms of BP are BP-I (severe bipolar mood disorder) and SAD-M (schizoaffective disorder manic type), and are characterized by at least one full episode of mania, with or without episodes of major depression (defined by lowered mood, or depression, with associated disturbances in rhythmic behaviors such as sleeping, eating, and sexual activity). A milder form of BP is BP-II, bipolar mood disorder with hypomania and major depression. BP-I often co-segregates in families with more etiologically heterogeneous syndromes, such as unipolar major depressive disorder (MDD), which is a more broadly defined phenotype. See McInnes, L. A. and Freimer, N. B., Mapping genes for psychiatric disorders and behavioral traits, Curr. Opin. in Genet. and Develop., 5:376–381 (1995).

TREATMENT OF INDIVIDUALS WITH BIPOLAR MOOD DISORDER

An estimated 2–3 million people in the United States are affected by BP-I. Currently, individuals are typically evaluated for bipolar mood disorder using the clinical criteria set forth in the most current version of the American Psychiatric Association's *Diagnostic and Statistical Manual of Mental Disorders* (DSM). Many drugs have been used to treat individuals diagnosed with bipolar mood disorder, including lithium salts, carbamazepine and valproic acid. However, none of the currently available drugs is able to treat every individual diagnosed with severe BP-I (termed BP-I) and drug treatments are effective in only approximately 60–70% of individuals diagnosed with BP-I. Moreover, it is currently impossible to predict which drug treatments will be effective in particular BP-I affected individuals. Commonly, upon diagnosis affected individuals are prescribed one drug after another until one is found to be effective. Early prescription of an effective drug treatment is critical for several reasons, including the avoidance of extremely dangerous manic episodes and the risk of progressive deterioration if effective treatments are not found. Also, appropriate treatment may prevent depressive episodes in BP-I individuals; these episodes are also dangerous and are characterized by a high suicide rate. The high prevalence of the disorder, together with frequent occurrence of hospitalizations, psychosocial impairment, suicide and substance abuse, has made BP-I a major public health concern.

Genetic Basis for Bipolar Mood Disorder

Mapping genes for common diseases believed to be caused by multiple genes, such as BP-I, may be complicated by the typically imprecise definition of phenotypes, by etiologic heterogeneity, and by uncertainty about the mode of genetic transmission of the disease trait. With psychiatric disorders there is even greater ambiguity in distinguishing between individuals who likely carry an affected genotype from those who are genetically unaffected. For example, one can define an affected phenotype for BP by including one or more of the broad grouping of diagnostic classifications that constitute the mood disorders: BP-I, SAD-M, MDD, and BP-II.

Thus, one of the greatest difficulties facing psychiatric geneticists is uncertainty regarding the validity of phenotype designations, since clinical diagnoses are based solely on clinical observation and subjective reports. Also, with complex traits such as psychiatric disorders, it is difficult to genetically map the trait-causing genes because: (1) the BP-I phenotype doesn't exhibit classic Mendelian recessive or dominant inheritance patterns attributable to a single genetic locus, (2) there may be incomplete penetrance i.e., individuals who inherit a predisposing allele may not manifest the disease; (3) the phenocopy phenomenon may occur, i.e., individuals who do not inherit a predisposing allele may nevertheless develop the disease due to environmental or random causes; (4) genetic heterogeneity may exist, in which case mutations in any one of several genes may result in identical phenotypes.

The existence of one or more major genes associated with BP-I and with a clinically similar diagnostic category, SAD-M (schizoaffective disorder manic subtype), is supported by segregation analyses and twin studies (Bertelson et al., 1977; Freimer and Reus, 1992; Pauls et al., 1992). However, efforts to identify the chromosomal location of BP-I genes have yielded disappointing results in that reports of linkage between BP-I and markers on chromosomes X and 11 could not be independently replicated nor confirmed in the re-analyses of the original pedigrees (Baron et al., 1987; Egeland et al., 1987; Kelsoe et al., 1989; Baron et al., 1993). Recent investigations have suggested possible localization of BP genes on chromosomes 18 (pericentromeric region) and 21q, but in both cases the proposed candidate region is not well defined and there is equivocal support for either location (Berrettini et al. (1994) Proc. Natl. Acad. Sci. USA, 91, 5918–5921, Murray, J. C., et al. (1994) Science 265, 2049–2054; Pauls et al., Am. J. Hum. Genet. 57:636–643 (1995); Maier et al., Psych. Res. 59:7–15 (1995); Straub et al., Nature Genet., 8:291–296 (1994)).

Despite abundant evidence that BP has a major genetic component, linkage studies have not yet succeeded in definitively localizing a BP gene. This is mainly because mapping studies of psychiatric disorders have generally been conducted under a paradigm appropriate for mapping genes for simple Mendelian disorders, namely, using linkage analysis in the expectation of finding high lod scores that definitively signpost the location of disease genes. The follow up to early BP linkage studies, however, showed that even extremely high lod scores at a single location can be false positives. See Egeland, et al., Nature 325:783–787 (1987); Baron et al., Nature 326:289–292 (1987); Kelsoe et al., Nature, 342:238–243 (1989); and Baron et al., Nature Genet. 3:49–55 (1993). These earlier studies used largely uninformative markers and did not use stringent criteria for identifying affected individuals.

LINKAGE DISEQUILIBRIUM ANALYSIS

Linkage disequilibrium (LD) analysis is a powerful tool for mapping disease genes and may be particularly useful for investigating complex traits. LD mapping is based on the following expectations: for any two members of a population, it is expected that recombination events occurring over several generations will have shuffled their genomes, so that they share little in common with their ancestors. However, if these individuals are affected with a disease inherited from a common ancestor, the gene responsible for the disease and the markers that immediately surround it will likely be inherited without change, or IBD ("identical by descent"), from that ancestor. The size of the regions that remain shared (i.e. IBD) are inversely proportional to the number of generations separating the affected individuals and their common ancestor. Thus, "old" populations are suitable for fine scale mapping and recently founded ones are appropriate for using LD to roughly localize disease genes. (Houwen et al., 1994, in particular FIG. 3 and accompanying text). Because isolated populations have typically had a small number of founders, they are particularly suitable for LD approaches, as indicated by several successful LD studies conducted in Finland (de la Chapelle, 1993).

LD analysis has been used in several positional cloning efforts (Kerem et al., 1989; MacDonald et al., 1992; Petrukhin et al., 1993; Hastbacka et al., 1992 and 1994), but in each case the initial localization had been achieved using conventional linkage methods. Positional cloning is the isolation of a gene solely on the basis of its chromosomal location, without regard to its biochemical function. Lander and Botstein (1986) proposed that LD mapping could be used to screen the human genome for disease loci, without conventional linkage analyses. This approach was not practical until a set of mapped markers covering the genome became available (Weissenbach et al., 1992). The feasibility of genome screening using LD mapping is now demonstrated by the applicants.

Identification of the chromosomal location of a gene responsible for causing severe bipolar mood disorder can facilitate diagnosis, treatment and genetic counseling of individuals in affected families.

Due to the severity of the disorder and the limitations of a purely phenotypic diagnosis of BP-I, there is a tremendous need to genetically subtype individuals with BP-I to confirm clinical diagnoses and to determine appropriate therapies based on their genotypic subtype.

The present invention comprises using genetic linkage and haplotype analysis to identify an individual having a bipolar mood disorder gene on the long arm of chromosome 18 (18q). In addition, the present invention provides markers linked to a gene responsible for susceptibility to bipolar mood disorder that will enable researchers to focus future analysis on that small chromosomal region and will accelerate the sequencing of a bipolar mood disorder gene located at 18q.

SUMMARY OF THE INVENTION

The present invention is directed to methods of detecting the presence of a bipolar mood disorder susceptibility locus in an individual, comprising analyzing a sample of DNA for the presence of a DNA polymorphism on the long arm of chromosome 18 between the markers D18S469 and D18S554, wherein the DNA polymorphism is associated with a form of bipolar mood disorder. The invention includes the use of genetic markers in the roughly 6–7 cM region between the markers D18S469 and D18S554 on 18q, inclusive, to genetically diagnose bipolar mood disorder in individuals and to confirm phenotypic diagnoses of bipolar mood disorder.

In a further embodiment, the invention provides methods of classifying subtypes of bipolar mood disorder by identifying one of more DNA polymorphisms located within the region between markers D18S469 and D18S554, inclusive, and analyzing DNA samples from individuals phenotypically diagnosed with bipolar mood disorder for the presence or absence of one or more of said DNA polymorphisms.

In yet a further embodiment, the methods of the invention include a method of treating an individual diagnosed with bipolar mood disorder comprising identifying one or more DNA polymorphisms located within 18q region between markers D18S469 and D18S554, and analyzing DNA samples from individuals phenotypically diagnosed with bipolar mood disorder for the presence or absence of one or more of the DNA polymorphisms, and selecting a treatment plan that is most effective for individuals having a particular genotype within the 6–7 cM region of chromosome 18.

BRIEF DESCRIPTION OF THE DRAWINGS

FIG. 2 is a table of lod scores for markers covering the entire human genome that exceeded the arbitrary coverage thresholds. Lod scores are shown for markers on chromosome 18, including one marker in the vicinity of the 18q22-q23 region: D18S1161.

FIG. 5A: Affected members of two families CR001 and CR004 with depiction of the shared marker haplotypes observed. The unshaded area outlined in solid lines is the more extensive haplotype conserved in CR004, the unshaded area outlined in dashed lines is the more extensive haplotype conserved in CR001. The shaded area indicates a haplotype that extends from D18S1009 to D18S554 and is common to both larger haplotypes. The ID numbers in the first column refer to the pedigree displayed in FIG. 1. In the remaining columns are the allele sizes at the indicated markers. "*" indicates an uncertain haplotype, "#" indicates that individual received two copies of the shaded haplotype (both haplotypes are displayed); "@" indicates an inferred haplotype. The markers used for haplotyping are shown at the top of the figure with inter-marker distances in cM. The marker order towards qter, is: D18S64, D18S55, D18S61, D18S485, D18S870, D18S469, D18S1161, D18S1121, D18S1009, D18S380, D18S554, D18S462, D18S461, D18S70. FIG. 5B: The other haplotypes that could be unambiguously reconstructed in the pedigree in FIG. 1 are shown. Those that are present in affected individuals are indicated by the ID numbers at the left of the diagram. "NT" indicates that an individual was not typed for a given marker.

DESCRIPTION OF SPECIFIC EMBODIMENTS

Figure 1A:
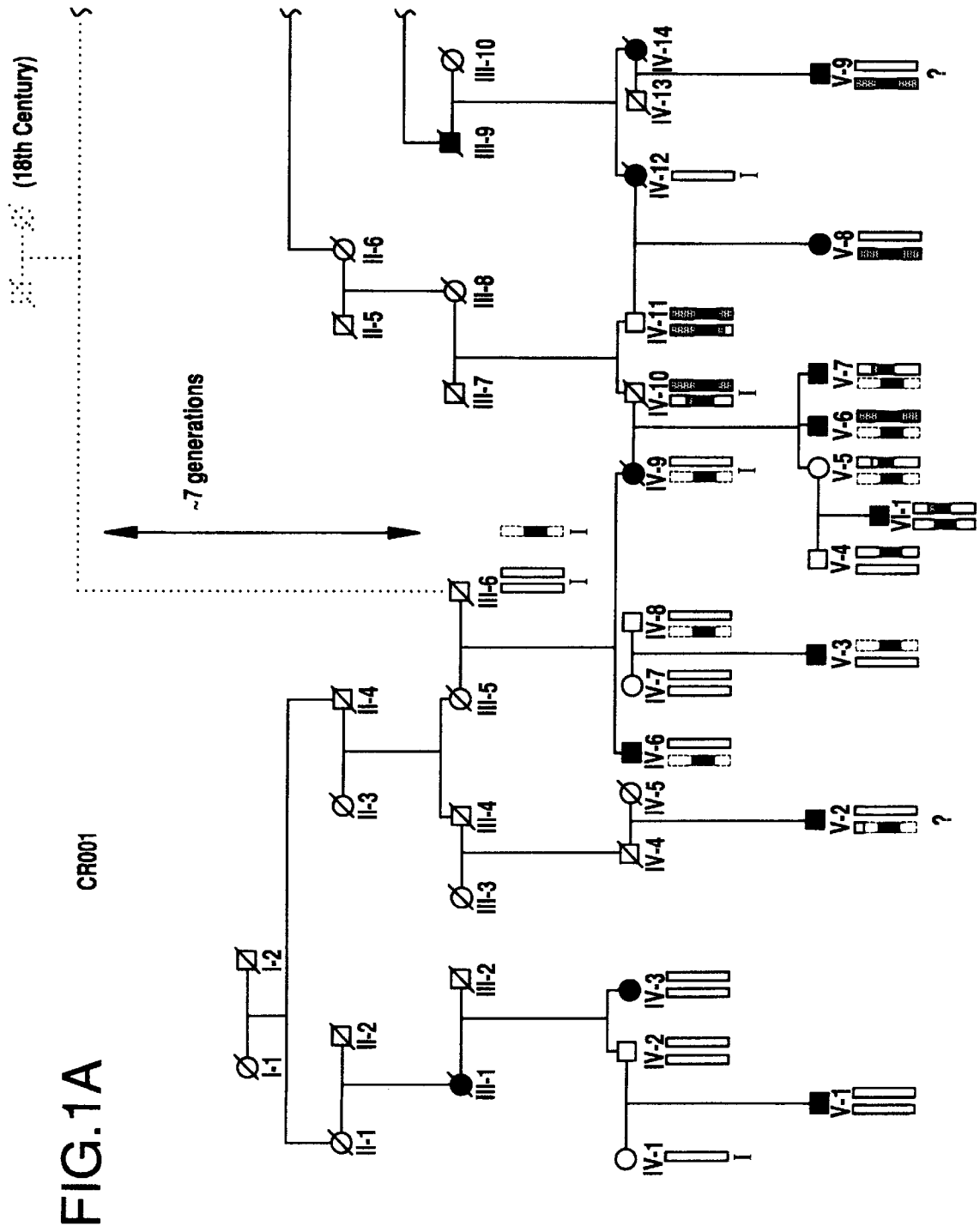
FIG. 1 is a pedigree chart showing two families, CR001 and CR004. Affected individuals are denoted by black symbols, deceased individuals by a diagonal slash. A schematic of each individual's haplotype (where available) is shown below the ID number. Recombinations are denoted by "–x"; consanguineous marriages by a double bar, and the conserved haplotype as black shading within the haplotype bars. The larger conserved region for CR004 is stippled, the larger conserved region for CR001 is indicated by a dashed outline. A "I" underneath the haplotype bars indicates inferred haplotype. A "?" indicates phase is uncertain. The connection between CR001 and CR004, dating to an 18th Century founding couple, is indicated by the dashed lines joining individuals III-6 and I4.

The recent availability of highly polymorphic, genetically mapped markers covering the human genome (Weissenbach, J., et al. (1996) Nature 359, 794–801, Murray, J. C., et al. (1994) Science 265, 2049–2054, Gyapay, G., et al. (1994) Nature Genet 7,246–339) has enabled the development of a multi-stage paradigm for mapping genes for complex traits. In the first stages, complete genome screening (e.g. through lod score analysis) is used to identify possible localizations for disease genes. Subsequently, the regions highlighted by the screening study are more intensively investigated to confirm the initial localizations and delineate clear candidate regions. Finally, fine mapping methods (such as haplotype or linkage disequilibrium (LD) analysis) or candidate gene approaches are used for positional cloning of disease genes.

Our genome screening study for BP employed the following strategies. Unlike previous genetic studies of BP, only those individuals with the most severe and clinically distinctive forms of BP (BP-I and schizoaffective disorder manic type, SAD-M were considered as affected, rather than including those diagnosed with a milder form of BP (BP-II) or with unipolar major depressive disorder (MDD). Two large pedigrees (CR001 and CR004) were selected from a genetically homogeneous population, that of the Central Valley of Costa Rica (as described in Escamilla, M. A., et al., (1996) Neuropsychiat. Genet. 67, 244–253, and in Freimer, N. B., et al. (1996) Neuropsychiat. Genet. 67, 254–263, both incorporated by reference herein). The entire human genome was screened for linkage using mapped microsatellite markers and a model for genetic analysis in which most of the linkage information derived from affected individuals. The goal of this stringent linkage analysis was to identify all regions potentially harboring major genes for BP-I in the study population. Empirically determined lod score thresholds (using linkage simulation analyses) were derived, to suggest regions worthy of further investigation.

Identification of all suggestive regions and weighing the relative importance of findings required complete screening of the genome. The coverage approach was developed to gauge the progress of this effort. Conventionally, the thoroughness of genome screening is evaluated by excluding genome regions from linkage under given genetic models. This approach, which is highly sensitive to misspecification of genetic models, maybe poorly suited for genome screening studies of complex traits; it is tied to the expectation of finding linkage at a single locus and demonstrating absence of linkage at all other locations in the genome. Additionally, exclusion analyses do not differentiate between genome regions where linkage is not excluded because markers are uninformative in the study population from those in which the genotype data are simply ambiguous. In contrast, the coverage approach is designed for studies aimed at genome screening rather than for studies whose goal is to demonstrate a single unequivocal linkage finding, and it provides explicit data regarding the informativeness of markers in the study pedigrees. Its use lessens the possibility that one would prematurely dismiss a given genome region as being unpromising for further study.

Because the exact genetic length of chromosomes is not clearly established, it is impossible to be certain that one has screened the entire genome. Although we report coverage of about 94% of the genome (under the 90%) dominant model) at the thresholds described above, this probably represents an underestimate. The remaining coverage gaps in our study occur predominantly at or near telomeres; as the upper bound estimates for the length of each chromosome were used, it is likely that the actual coverage gaps in these regions are smaller than or conservative assessment.

The presence of consistently positive lod scores over a given region was considered to be of greater significance than isolated peak lod scores. Such clustering suggests true co-segregation of markers and phenotypes (i.e. alleles are shared identical by descent rather than identical by state) and is more readily observed in analyses of a few large pedigrees (as in our study) than in examination of several smaller families. The data presented herein indicates clustering of positive lod scores in the region of the 18q22-q23. The screening data provide obvious indication of a BP-I susceptibility locus in 18q22-q23 as suggestive lod (logarithm of odds) scores were obtained there over a region of about 40 cM.

The genome screen was conducted in two stages. The Stage I screen identified areas suggestive of linkage, so that those areas could be saturated with available markers, and so that regions, referred to as 'coverage gaps,' could be pinpointed where markers were insufficiently informative in our sample to detect evidence of linkage. The Stage II screen followed up on regions flanking each marker that yielded peak lod scores approximately equal to or greater than the thresholds used for the coverage calculations, which were deemed regions of interest, and filled in coverage gaps. The results of the complete genome screen (Stages I and II) using 473 markers is described below.

In addition, linkage disequilibrium analysis of an independently collected sample of 48 unrelated BP-I patients was conducted. These patients were from the same ancestral population as the patients in the CR001 and CR004 pedigrees. LD analysis of further BP-I patients from the CRCV with markers in this 18q23 region is conducted to confirm and fine map a BP-I gene in this region. This approach, using additional BP-I patients from this CRCV population and additional markers identifies the region of maximum LD and can precisely localize a BP-I susceptibility gene.

A conservative approach to linkage analysis was used in that almost all of the information for linkage is derived from individuals with a severe, narrowly defined phenotype. While this approach made it very unlikely that lod scores greater than conventional thresholds of statistical significance (e.g. _>3) would be obtained, it provided confidence in the robustness of the most suggestive findings.

Three lines of evidence support the localization of a BP-I susceptibility locus to 18q22-q23: association analyses, linkage analyses, and direct observation of a conserved marker haplotype.

Screening Lod Score Analyses

Linkage analysis was performed using a narrow definition of the affected phenotype and a conservative model of genetic transmission. In particular, a high rate of phenocopies (non-genetic cases) was estimated. In an initial genome screen, two-point lod score analysis was conducted for all markers (Lathrop et al., 1984; Ott, 1991; Terwilliger and Ott, 1994) and it was observed that all of the markers tested in 18q22-q23 displayed positive maximum lod scores (D18S64: 1.89 at recombination fraction ($\theta$)=0.18, D18S55: 1.45 at $\theta$=0.18, D18S61: 1.75 at $\theta$=0.16, and D18S70: 0.76 at $\theta$=0.20). This suggestive evidence for linkage was obtained over a greater chromosomal length (at least 40 centiMorgans (cM)) than in any other genome region. Eighteen additional microsatellite loci that cover the 18q22-q23 region at intervals of 0–5 cM were typed and linkage analyses were performed using the model employed for the initial genome screening studies. Fourteen of the markers, spaced across the region, displayed positive maximum lod scores (with six markers having lod scores >1.0), with no peak localization. These results supported a localization of a BP-I gene in this region of chromosome 18.

Association Analyses

To further evaluate the evidence for this localization, an independent method was utilized which does not rely on specifying the mode of genetic transmission for BP-I. In isolated populations, it has previously been shown that the identification of genome regions where marker allele frequencies differ between patients and the background population can be used to map disease loci (Friedman et al., 1995). When such deviation is based on a substantially increased frequency of one or a few alleles in the patients, the region is almost certainly inherited identical by descent ("IBD"), with the disease gene, from common ancestors. The genome screening experiments followed the procedures described by Boehnke, 1991 for directly estimating allele frequencies using genotypes from the family members in the study. For many of the markers tested in 18q23, the alleles most commonly observed in the BP-I patients are rare in the reference families of the Centre d'Etude du Polymorphisme Humain (CEPH), which are drawn from a variety of Caucasian populations (Dausset et al., 1990). For example, an allele at D18S70 of 124 basepairs in length was observed in 16 out of 24 BP-I individuals tested but in only 3% of the chromosomes from the CEPH population.

To evaluate whether these differences in allele frequency could simply be explained by genetic drift, a set of individuals sampled from the general Costa Rican population was genotyped using the 18q23 markers as well as a series of microsatellites (from other genome regions) that have been employed in comparative studies of several populations (Di Rienzo et al., 1994; Garza et al., 1995). The Costa Rican reference sample showed no significant deviations from Hardy-Weinberg equilibrium for these markers, nor were there significant differences in allele frequency with other human populations (E. Rojas et al., unpublished observations). The marker allele frequencies for the patient sample were compared with the Costa Rican reference sample, without making any assumptions concerning linkages. For several of the 18q23 markers (D18S469, D18S554, D18S461, and D18S70), allele frequencies in the BP-I pedigree sample were highly significantly different from those in the Costa Rican population, but no such differences were observed for the markers from other genome regions.

Revised Lod Score Calculations

As allelic associations may profoundly affect the results of lod score calculations new linkage analyses using only affected individuals were carried out for the 18q23 markers, correcting for the observed significant associations between BP-I and several of the marker alleles. The lod scores obtained for several of these markers (D18S380, D18S554, D18S461, and D18S70) provide independent support for the localization of a BP-I gene to this region, as indicated, for example, by marker D18S380 which yielded evidence of linkage but did not display significant allelic association with BP-I.

Conserved Marker Haplotypes

Figure 1B:
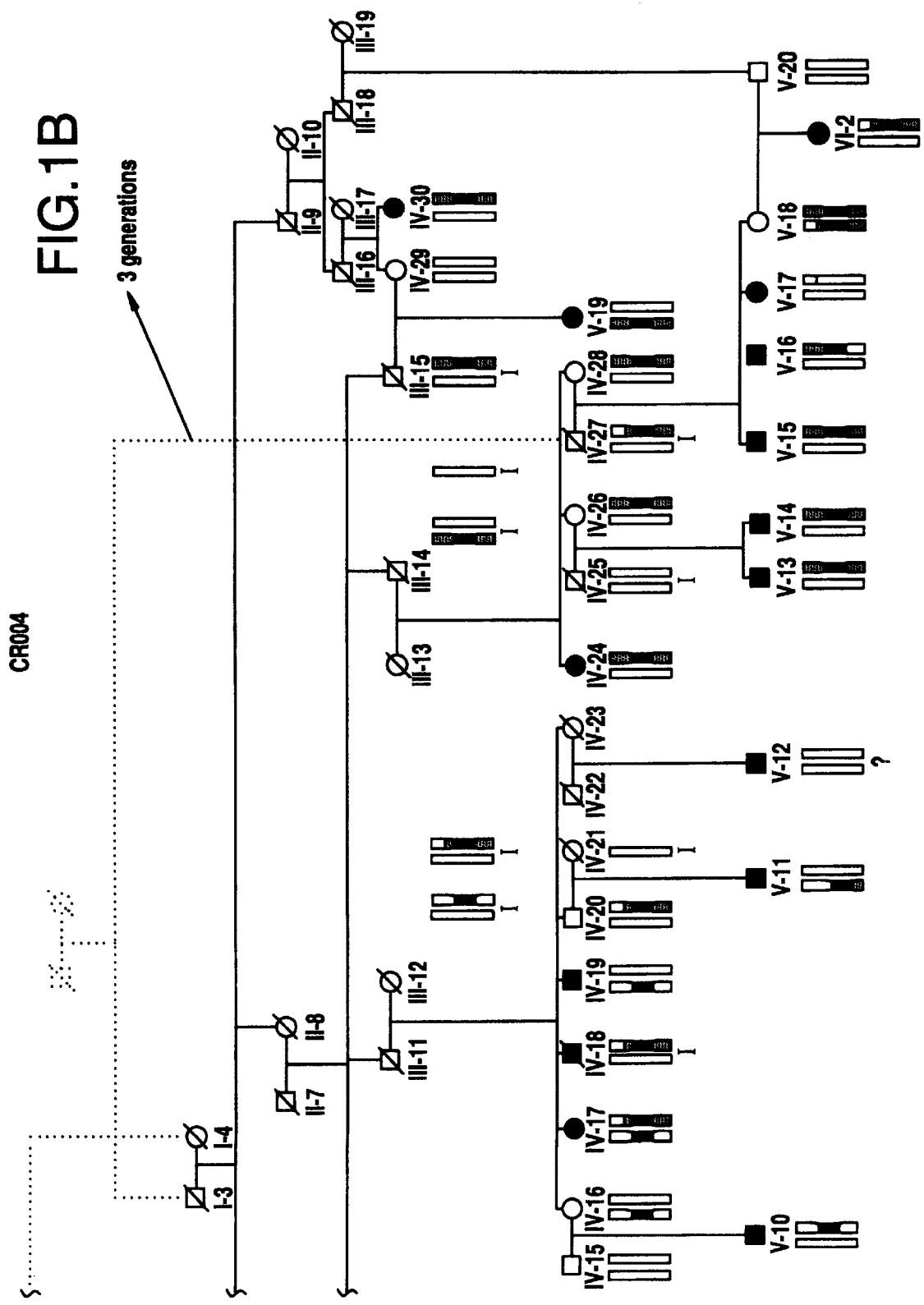

The suggestion that a gene for BP-I is located in the 18q22-q23 region is further strengthened by the observation that BP-I segregates with particular marker haplotypes in both families (FIGS. 1 and 5A and 5B). 18q22-q23 marker haplotypes for all genotyped individuals (and for deceased individuals whose genotypes could be reconstructed), BP-I segregates with particular marker haplotypes in both families (FIGS. 1, 5A and 5B). In CR004, 16 of 17 affected individuals share portions of a marker haplotype from D18S64 to D18S70, a distance of about 40 cM (FIGS. 5A and 5B), with the majority of these individuals sharing at least 30 cM in common. Most affected individuals in CR004 share the distal segment of this haplotype, consisting largely of marker alleles that are rare in the general population of Costa Rica, indicating that the segment is inherited IBD from a common ancestor. A distinct, similarly sized haplotype is shared by seven of the nine BP-I individuals in CR001 (FIG. 5A). An identical haplotype, however, is observed in both families, in the region between D18S469 and D18S554 (a distance of about 6–7 cM). Of the BP-I individuals whose genotypes could be fully reconstructed, 22 out of 26 apparently share portions of this high-risk haplotype. Of the four BP-I individuals who do not display this haplotype sharing (FIG. 1, individuals IV-3, V-1, V-2, and V-12), three do not descend from a founding couple who lived in the 18th Century and were ancestral to the main branches of CR001 and CR004. As the interval between D18S469 and D18S554 demonstrates sharing of a marker haplotype among most of the distantly as well as closely related BP-I individuals, the locus for BP-I susceptibility is probably within this six to seven cM segment. Probable recombinations in this interval in two individuals in CR004 (V-16 and V-17) were also identified.

It is evident that the high risk haplotypes were introduced into the BP-I families through several ancestors, who were themselves distantly related to each other (FIG. 1). Although the BP-I patients studied are members of families that share common ancestry, the two pedigrees have been separated for at least seven generations. It is to be expected that such distantly related patients would share IBD a region of several cM surrounding a BP-I susceptibility gene but extremely unlikely that they would share a segment of this size in any other area of the genome.

Direct visual inspection is the best means of evaluating the evidence from multiple transmissions of a disease allele. Identifying such marker haplotypes facilitates mapping of disease loci when locus heterogeneity exists within extended pedigrees. The probability of locus (and ancestral) homogeneity increases when one samples families from relatively isolated populations. It is likely, however, that over several generations, many distantly related individuals will marry into such pedigrees, and thus the same disease allele (and a conserved marker haplotype surrounding the disease locus) may be introduced several times, and some individuals will be homozygous for rare alleles.

Examination of the pedigrees studied clearly indicates multiple entries of a high risk haplotype in 18q22-q23. Portions of this haplotype occur in almost all patients in both pedigrees. Linkage analysis does not recognize the information conveyed by haplotypes shared via distant familial connections unless all relations are exactly specified and all markers are included in a single analysis; this would lead to unacceptable calculation times. In addition, such analyses generally do not sufficiently localize disease genes to permit positional cloning efforts. In contrast, identifying the region of maximal sharing of a marker haplotype in an isolated population can pinpoint the location of a gene for a complex disorder, even when the haplotype is observed in only a subset of patients (Nystrom-Lahti, et al., 1994). Extended haplotypes, such as those observed, thus yield largely independent evidence for disease gene localization, corroborating the results of lod score and association analyses, and indicate regions to be highlighted in further mapping studies.

Because the Costa Rican population is descended from only a small number of ancestors (M. Escamilla et al., unpublished data) the localization of the BP-I susceptibility gene will be narrowed with additional BP-I samples from this population using linkage disequilibrium (LD) methods. Such an approach was recently used to follow up initial localization of a gene for insulin dependent diabetes mellitus (Davies et al., 1994; Copeman et al., 1995). For this reason examination of a sample of "unrelated" BP-I patients from the Costa Rican population is expected to more precisely localize the putative BP-I gene by identifying the region of maximum LD (Lander and Shork, 1994; Puffenberger et al. 1994b; Collins, 1995).

As predicted by prior genetic epidemiological studies, and by the segregation patterns of BP-I within extended pedigrees in which many apparent carriers are themselves unaffected, the high risk haplotype observed in CR001 and CR004 demonstrates incomplete penetrance (for example individual IV-26 is not affected with BP-I but apparently transmits illness to two sons). Although final diagnoses have been assigned to all identified members of CR001 and CR004 with BP-I and SAD-M, final diagnoses have not been to all members of these families. However, of those individuals who have been assigned final diagnoses other than BP-I and SAD-M, the shared marker haplotype is observed in all six of the individuals with BP-II (bipolar disorder with hypomania and major depression), MDD (major depressive disorder), or organic mood disorder. Six of eleven individuals with no apparent psychiatric diagnosis share this haplotype, however four of them transmit the haplotype (and presumably the risk of BP-I) to affected offspring. Precise delineation of penetrance in these families may not be possible until causative mutations are identified, as was recently demonstrated in pedigrees loaded for Hirschsprung's disease (Puffenberger et al. 1994b).

The invention now being generally described, the following examples are provided for purposes of illustration only and are not to be considered to limit the invention.

EXAMPLES

PEDIGREES

Two independently ascertained Costa Rican pedigrees (CR001 and CR004) were chosen because they contained a high density of individuals with BP-I and because their ancestry could be traced to the founding population of the Central Valley of Costa Rica. The current population of the Central Valley (consisting of about two million people) is predominantly descended from a small number of Spanish and Amerindian founders in the 16th and 17th centuries Escamilla, M. A., et al., (1996) Neuropsychiat. Genet. 67, 244–253. Studies of several inherited diseases have confirmed the genetic isolation of this population (Leon, P., et al. (1992) Proc. Natl. Acad. Sci. USA. 89,5181–5184, Uhrhammer, N., et al. (1992) Am. J. Hum. Genet. 57, 103–111). An extensive description of pedigrees CR001 and CR004 is provided in a separate paper (Freimer, N. B., et al. (1996) Neuropsychiat. Genet. 67, 254–263). In the course of the study, two links between these pedigrees were discovered separately, however, because these links were discovered after the simulation analyses were completed and after the genome screening study had been initiated.

All available adult members of these families were interviewed in Spanish using the Schedule for Affective Disorders and Schizophrenia Lifetime version (SADS-L) (Endicott, J. et al, (1978) Arch. Gen. Psych. 35, 837–844). Individuals who received a psychiatric diagnosis were interviewed again in Spanish by a research psychiatrist using the Diagnostic Interview for Genetic Studies (DIGS) (Numberger, J. L. et al. (1994) Arch. Gen. Psychiat. 51, 849–859). This recently developed instrument is similar to, but more detailed than SADS-L. The interviews and medical records were then reviewed by two blinded best estimators who reached a consensus diagnosis. The diagnostic procedures are described in detail in Freimer, N. B., et al. (1996) Neuropsychiat. Genet. 67, 254–263 (incorporated by reference herein).

UNRELATED CRCV BP-I PATIENT STUDY

BP localizations obtained through the CRCV pedigree studies were confirmed by genotyping an independently collected sample of 48 unrelated BP-I patients from the CRCV. In this fine mapping LD analysis, 48 unrelated BP-I patients from the CRCV were identified and genotyped using microsatellite markers spaced at narrow intervals across chromosome 18. As these patients are descended from the same ancestral population as the patients in the pedigrees previously studied (CR001 and CR004), many of them should share disease susceptibility alleles inherited identical by descent (IBD) from one or a few common ancestors, and linkage disequilibrium (LD) should be present at marker loci surrounding the disease genes.

The sample of 48 BP-I patients included 25 women and 23 men who were recruited from psychiatric hospitals and clinics in the CVCR. These patients were ascertained only on the basis of diagnosis and CV ancestry, and were not selected on the basis of history of BP illness in family members. A structured interview of each patient was conducted by a psychiatrist, and medical and hospital records were collected. Ascertainment and diagnostic procedures were as described above. However, in order to further lessen the probability of phenocopies among this unrelated sample, for which we lacked pedigree information, the affected phenotype was defined even more narrowly than in the pedigree study. Individuals considered affected in this study had to have suffered at least two disabling episodes of mania (requiring hospitalization) and a first onset of the illness before age 45.

Genealogical research on each of the 48 BP-I patients confirmed that on average, 70% of their great-grandparents were born in the CRCV. Individuals whose great-grandparents were born in the CRCV were considered likely to be descended from the original Spanish and Amerindian founders of the CRCV. Genealogical research showed that 2 patients are first cousins and the remaining 46 have no relationship within the past 4 generations.

GENOTYPING PEDIGREE STUDIES

Linkage simulations were used to select the most informative individuals from pedigrees CR001 and CR004 for genotyping studies (Freimer, N. B., et al. (1996) Neuropsychiat. Genet. 67, 254–263). Under a 90% dominant model, simulation analyses with these individuals suggested that evidence of linkage would likely be detected (e.g. a probability of 92% of obtaining lod >1.0 in the combined data set) using markers with an average heterozygosity of 0.75 spaced at 10 cM intervals (as discussed in 24)). For the Stage I screen, the most polymorphic markers (307 in total) were chosen, placed at approximately 10 cM intervals on the 1992 Genethon map (Houwen, R., et al. (1992) Nature 359, 794–801). These markers were then supplemented by a small number of markers from the Cooperative Human Linkage Center (CHLC) public database. For the Stage II screen, 166 markers were added from newer Genethon and CHLC maps as they became available (Murray, J. C. et al. (1994) Science 265, 2049–2054, Gyapay, G., et al. (1994) Nature Genet. 7,246–339) and from the public database of the Utah Center for Genome Research, all of which are publicly available. DNA samples (from individuals in the CEPH families) that were used for size standards for Genethon and CHLC markers were included in the experiments to permit comparison of allele sizes between members of the CRCV population and individuals in the CEPH database. Marker D18S1009 is a previously unpublished Genethon marker, however information about this marker is now available from the Genome Database.

Genotyping procedures were as described previously DiRienzo, A. et al. (1994) Proc. Natl. Acad. Sci. USA 91, 3166–3170 (incorporated by reference herein). Briefly, one of the two PCR primers was labeled radioactively using a polynucleotide kinase and PCR products were run on polyacrylamide gels. Autoradiographs were scored independently by two raters. Data for each marker were entered into the computer database twice and the resultant files were compared for discrepancies.

Association Analysis

Associations between markers on 18q23 and bipolar disease were assessed by comparing the frequency of marker alleles as estimated from affected individuals in the families with the frequency of marker alleles in the Costa Rican reference population. Marker allele frequencies were first estimated on a combined data set including the bipolar patients in the pedigrees (with correction for dependency due to family relationships as per Boehnke 1991) and the population sample. Alleles that were rare in the combined data set were collapsed into a single allele for each marker, until no alleles with a frequency of less than 4% remained, to prevent chance occurrence of rare alleles from having disproportionate effects in subsequent comparisons. Following this recoding, allele frequencies were again estimated on the combined data. Marker allele frequencies were then estimated separately in the reference population and in affected family members. A similar procedure was used by Schellenberg et al. (1987). The likelihood obtained in analyzing the combined data was compared with the product of the likelihoods obtained in the separate analyses, to test the null hypothesis of no difference between allele frequencies in the Costa Rican reference sample and affected individuals from the BP-I families. Under the null hypothesis, this likelihood ratio statistic is distributed as a Chi-square random variable with n-1 degrees of freedom, where n indicates the number of alleles for the marker.

Haplotype Construction

Haplotypes for the pedigrees in 18q were constructed by hand, without knowledge about the diagnostic status of family members. A minimum recombination strategy was the parsimonious method chosen to guide haplotype construction. Three individuals who carry diagnoses of BP-I or SAD-M are deceased but their haplotypes could be partially (IV-12) or nearly fully reconstructed (IV-9, IV-18). The haplotype information is presented schematically in FIGS. 5A and 5B. Only BP-I and SAD-M individuals and their direct ancestors are depicted. As indicated in the discussion of the conserved haplotypes, there is no adequate means to statistically represent the evidence deriving from such transmission.

Definition Of The Boundaries Of The Candidate Region By Additional Marker Typing Studies Statistical analysis suggested a BP-I localization in 18q23-qter, but the strongest evidence derives from an extended marker haplotype that is shared by most of the BP-I patients in the pedigree study, particularly in Family CR004. This haplotype also helps define a candidate region for the additional mapping.

Genetic approaches, as described below, are used to aim for a BP-I candidate region of less than one Mb. As new markers are tested, and increased haplotype sharing is identified, one moves closer to the causative gene (Puffenburger, 1994a).

The most likely region for a BP-I locus is between markers D18S469 and D18S554, a distance of 7 cM. This location is suggested by recombination events that appear to interrupt the conserved haplotype in Family CR004. Most patients share a haplotype from D18S554 towards the telomere (marker D18S70), and the majority share a haplotype from above D18S469 to D18S70. However, two patients share only the centromeric portion of the haplotype (a total of 12 markers covering more than 15 cM); that is, there is a "break" below D18S469. Additional possible evidence for this location is provided by two of the three affected individuals in CR004 who do not share the extended haplotype observed in the other patients. These individuals may share this haplotype at markers D18S469 and D18S554.

An additional six markers from Généthon have been mapped within D18S469 and D18S554 dividing the interval into one to two cM segments. A further set of new markers has also been mapped to this region, by the CHLC (1994). All of the available Généthon and CHLC markers are used to genotype DNA from the previously investigated individuals from CR001 and CR004. From these experiments a refined region of maximal haplotype sharing is delineated. In addition, IBD and IBS sharing is distinguished for the patients who currently possess "BP-I" alleles only for markers D18S469 and D18S554.

It is expected that the above described experiments will delineate a likely candidate region of as small as one cM, permitting initiation of physical mapping and cloning studies. However, it is necessary to enlarge the study sample and to identify additional markers in order to proceed with the detailed mapping of this region.

For all of the genotyping studies used to characterize a putative BP-I locus in the 18q23-qter chromosomal region, standard procedures (Di Rienzo et al., 1994) are used. One of the PCR primers is radioactively labeled with P32 using T4 kinase, and the PCR products are size separated using denaturing sequencing gels and detected by autoradiography. The sizes of alleles are determined to the level of a single base pair by comparison with known standards (Di Rienzo et al., 1994).

GENOTYPING OF UNRELATED BP-I CRCV PATIENTS

Twenty-seven markers were used to genotype all 48 individuals (as well as 53 individuals used to establish genetic phase) at approximately 5 cM intervals along the entire chromosome 18. It was hypothesized that such a screen would permit the evaluation of evidence in the 18q22-q23 region and also to investigate other regions on chromosome 18 in which linkage to BP has been suggested by other groups in other populations. For each individual, two-marker haplotypes in each of the 26 inter-marker intervals were investigated. For 38 of the 48 BP-I patients, genotypes of parents or children were available to assist in phase determination. Because of phase ambiguities in the remaining 10 individuals, minimal and maximal two-marker haplotype sharing was evaluated as follows: (1) Minimal: the number of individuals (and chromosomes) who definitely shared a chromosomal segment defined by a particular pair of alleles (phase known chromosomes) and (2) Maximal: the number of individuals (and chromosomes) who could possibly share a chromosomal segment defined by a particular pair of alleles (includes phase unknown chromosomes). The threshold used to identify areas of high IBD sharing of chromosomes in this initial screen was designated as maximal sharing of a two-marker haplotype by 50% or more of the 48 individuals (or 25% or more of the 96 chromosomes).

Arbitrary thresholds were designated to identify possible areas of high IBD sharing among the 48 patients. Eight of the 26 regions passed this screen. Within each of these 3 regions, one to three additional markers were typed to permit detection of LD, if present, over regions of one to two cM.

A total of 42 chromosome 18 markers were used to genotype the study sample: D18S59, D18S1140, D18S476, D18S481, D18S391, D18S452, D18S843, D18S464, D18S1153, D18S378, D18S53, D18S453, D18S40, D18S66, D18S56, D18S57, D18S467, D18S460, D18S450, D18S474, D18S69, D18S64, D18S1134, D18S1147, D18S60, D18S68, D18S55, D18S477, D18S61, D18S488, D18S485, D18S541, D18S870, D18S469, D18S874, D18S1121, D18S380, D18S1009, D18S844, D18S554, D18S461, D18S70 (from pter to qter). Of these 42 markers, seven are located within the 18q22–23 region extending from the marker D18S469 to marker D18S554 (inclusive). This region is referred to as the 18q22-q23 region.

For each marker the likelihood that a particular allele (or alleles) is over-represented on disease chromosomes, as compared to non-disease chromosomes was evaluated. The results of this likelihood test provide a conservative but powerful measure of LD between two loci.

PEDIGREE STATISTICAL ANALYSES

Two-point linkage analyses were performed for all markers. Marker allele frequencies were estimated from the combined data set with correction for dependency due to family relationships (Boehnke, M. (1991) Am. J. Hum. Genet. 48, 22–25). The linkage analyses for Stages I and II included the 65 individuals who were genotyped as well as an additional 65 individuals who had been diagnostically evaluated but not genotyped. Only individuals with BP-I were considered affected with the exception of two persons, one in each family, who carry diagnoses of schizoaffective disorder manic type (SAD-M). The SAD-M individuals were included as affected because BP-I and SAD-M are often difficult to distinguish from each other based on their clinical presentation and course of illness (Goodwin, F. K. et al. (1990) in Manic Depressive Illness. (Oxford University Press, New York), pp. 373–401; Freimer, N. B et al. (1993) in The Molecular and Genetic Basis of Neurological Disease, pp. 951–965; Freimer, N. B. et al. (1996) Neuropsychiat. Genet. 67 254–263; and Freimer, N. B. et al (1996) Nature Genetics 12:436–441, all incorporated by reference herein). In all, 20 individuals were designated as affected within CR004 (Copeman, J. B., et al. (1995) Nature Genet. 9, 80–85 available for genotyping) and 10 individuals from CR001 (Kelsoe, J. R. et al. (1989) Nature 342, 238–243 available for genotyping). The phenotype for all other individuals was designated as unknown except for 17 individuals who were designated as unaffected because they had been thoroughly clinically evaluated, showed no evidence of any psychiatric disorder, and were well beyond the age of risk (50) for BP-I (linkage simulation studies indicated that these unaffected individuals contributed little information to the linkage analysis).

Linkage analyses were performed using a nearly dominant model (assuming penetrance of 0.81 for heterozygous individuals of 0.9 for homozygotes with the disease mutation). This model was chosen from five different single-locus models (ranging from recessive to nearly dominant) due to its consistency with the segregation patterns of BP in the two pedigrees and because it had demonstrated the greatest power to detect linkage in simulation studies Freimer, N. B., et al. (1996) Neuropsychiat. Genet. 67, 254–263. Based on Costa Rican epidemiological surveys Escamilla, M. A., et al., (1996) Neuropsychiat. Genet. 67, 244–253, the population prevalence of BP-I was assumed to be 0.015 (and thus the frequency of the disease allele was assumed to be 0.003)(based on epidemiological surveys in Costa Rica, Adis, G. (1992) "Disordenes mentales en Costa Rica: Observaciones Epidemiologicas," (San Jose, Costa Rica: Editorial Nacional de Salud y Seguridad Social)). The frequency of BP-I in individuals without the disease allele was conservatively set at 0.01 which effectively specified a population phenocopy rate of 0.67 (i.e. an affected individual in the general population has a ⅔ probability of being a phenocopy). For multiply affected families, the probability that a gene is segregating is highly increased, which implies that affected individuals in our study pedigree have a lower probability to be phenocopies than affected individuals in the general population, particularly those with several affected close relatives (the exact probabilities are dependent on the degree of relationship between patents and the number of intervening unaffected individuals). These parameters were chosen to ensure that most of the linkage information derives from affected individuals. The rationale for selecting these parameters and results of analyses that demonstrate the conservatism of this model are described by Freimer, N. B., et al. (1996) Neuropsychiat. Genet. 67, 254–263. The LINKAGE package (Lathrop et al., (1984) Proc. Natl. Acad. Sci. USA 81, 3443–3446) was used for lod score analysis and to obtain maximum likelihood estimates of the marker allele frequencies, taking into account the existing family relationships (see Boehnke, Am. J. Hum. Gent. 48, 22–25 (1991)).

UNRELATED BP-I CRCV PATIENT STATISTICAL ANALYSES

A likelihood test of disequilibrium (J. Terwilliger, Am. J. Hum. Genet. 56, 777 (1995)) was used to estimate a single parameter, lambda, that quantifies the over-representation of marker alleles on disease chromosomes as compared to non-disease chromosomes. We chose this method of analysis over another commonly used disequilibrium analysis method, the transmission disequilibrium test (TDT, R. Spielman et al., Am. J. Hum. Genet. 52, 506 (1993)) because data from all 48 BP-I patients could be used in the likelihood approach. Effective use of the TDT requires phase-known, heterozygous parental chromosomes. We do not have parental genotypes for 20 of the 48 BP-I patients. Simulations indicated that with our data, the likelihood test of disequilibrium would be more powerful than the TDT. Lambda has been shown to be a superior measure for LD fine mapping, compared to other frequently used measures, because it is directly related to the recombination fraction between the disease and the marker loci. Non-disease chromosomes were chosen from the phase-known chromosomes of parents, spouses and children of affected individuals, if available. Designation of chromosomes of family members as non-disease in a disorder such as BP-I, which is not fully penetrant, necessitates specifying a model of disease transmission. The same model of transmission was employed in this LD likelihood test as was used in the initial genome screen of the pedigrees CR001 and CR002 described herein. One parameter was specified differently from the genome screen: the phenocopy rate was set to zero in the LD likelihood analysis. A phenocopy rate was not specified in the transmission model because the effect of phenocopies will be "absorbed' by the lambda parameter, in that presence of phenocopies in our sample will serve to erode the association between marker alleles and disease, and hence reduce the estimate of lambda.

COVERAGE

To access coverage for a marker, the number of informative meioses at the estimated recombination fraction was calculated using the estimate of the variance (the inverse of the information matrix) (Petrukhin, K. E. et al. (1993) Genomics 15, 76–85). Alternatively, when the estimated frequency of recombination was close to 0 or 1, Edwards' equation was applied to calculate the equivalent number of observations (Edwards, J. H. (1971) Ann. Hum. Genet. 34, 229–250). These meioses represent the amount of linkage information provided by the marker, given the pedigree structure and the genetic model applied. Linkage to the marker in question was then assumed and the load score that would be observed as a disease gene is hypothetically moved in increments away from that marker was calculated. All regions around a marker that would have generated a lod score that exceeded our thresholds for possible linkage (0.8 in CR001, 1.2 in CR004, and 1.6 in the combined data) were considered covered. These lod score thresholds were derived from simulation analyses showing the expected distribution of lod scores under linkage and non-linkage Freimer, N.B., et al. (1996) Neuropsychiat. Genet. 67, 254–263, and approximately represent a result that is 250 times more likely to occur in linked simulations than in unlinked simulations. Coverage maps were constructed (FIGS. 5A and 5B) by superimposing the regions covered by each market on the genetic map of each chromosome. At the end of the Stage II screen, a total of 473 microsatellite markers had been typed with genome coverage (in the combined data set) of over 94%. Possible coverage gaps are indicated by unshaded areas and are mainly concentrated near telomeres. Because the coverage calculations make use of market informativeness within the pedigrees, the coverage approach thus permits detection of instances where markers with expected high heterozygosities are uninformative in our data set.

PEDIGREE LINKAGE ANALYSIS RESULTS

Figure 6A:
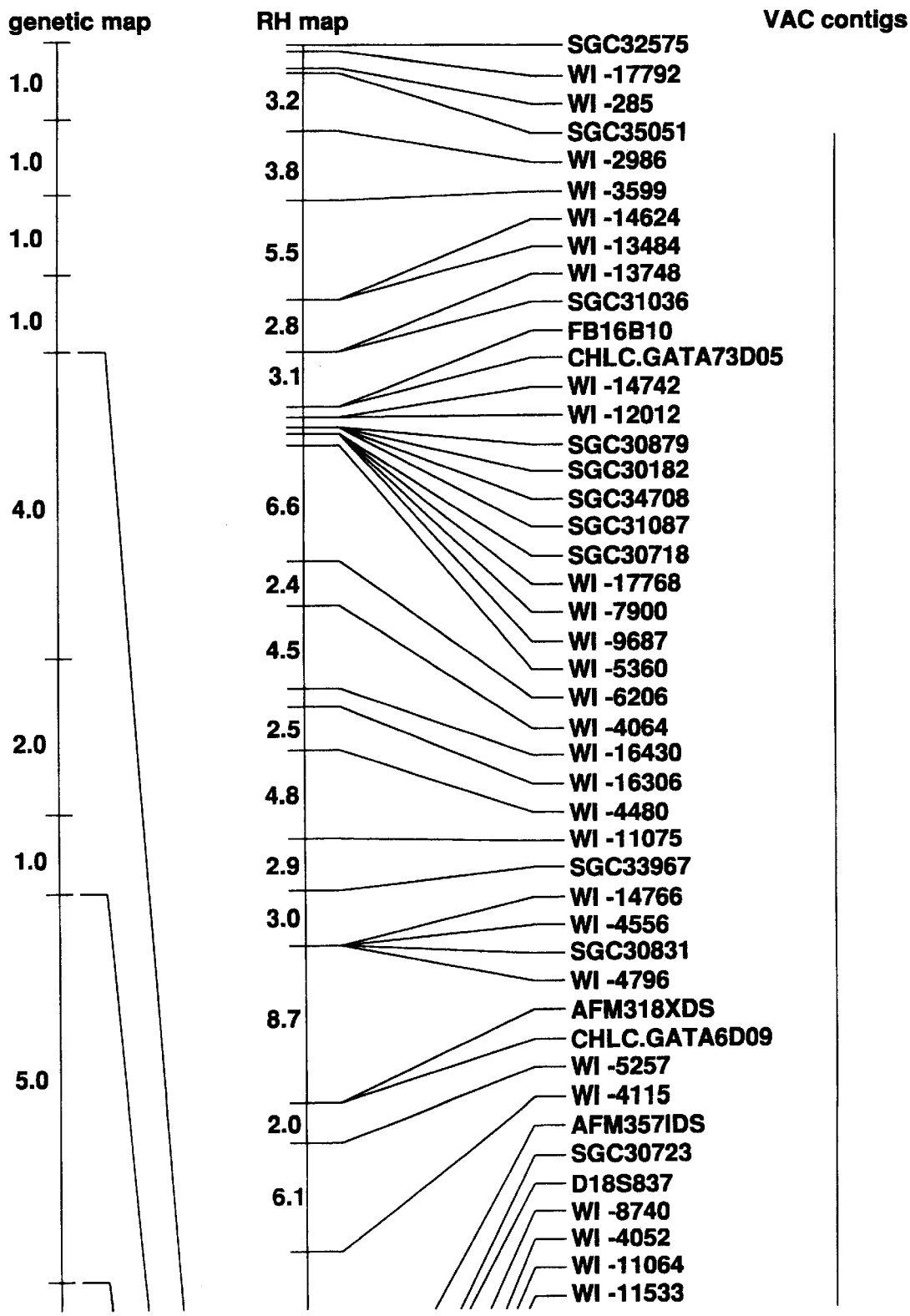
FIGS. 6A and 6B depicts publicly available markers in the 18q22-q23 region of chromosome 18 along with their locations on a genetic linkage map and the radiation hybrid map.
Figure 6B:
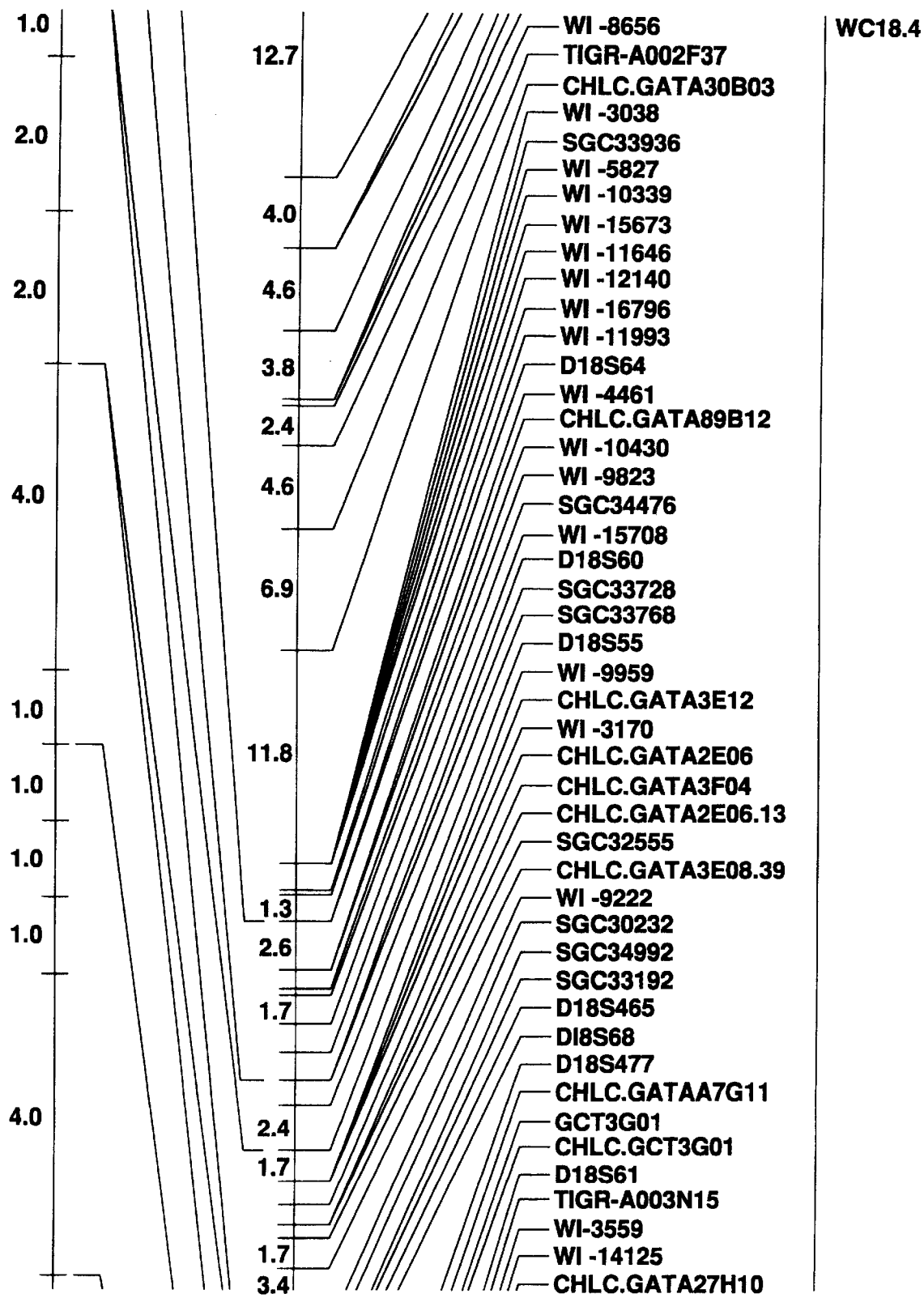
Figure 6C:
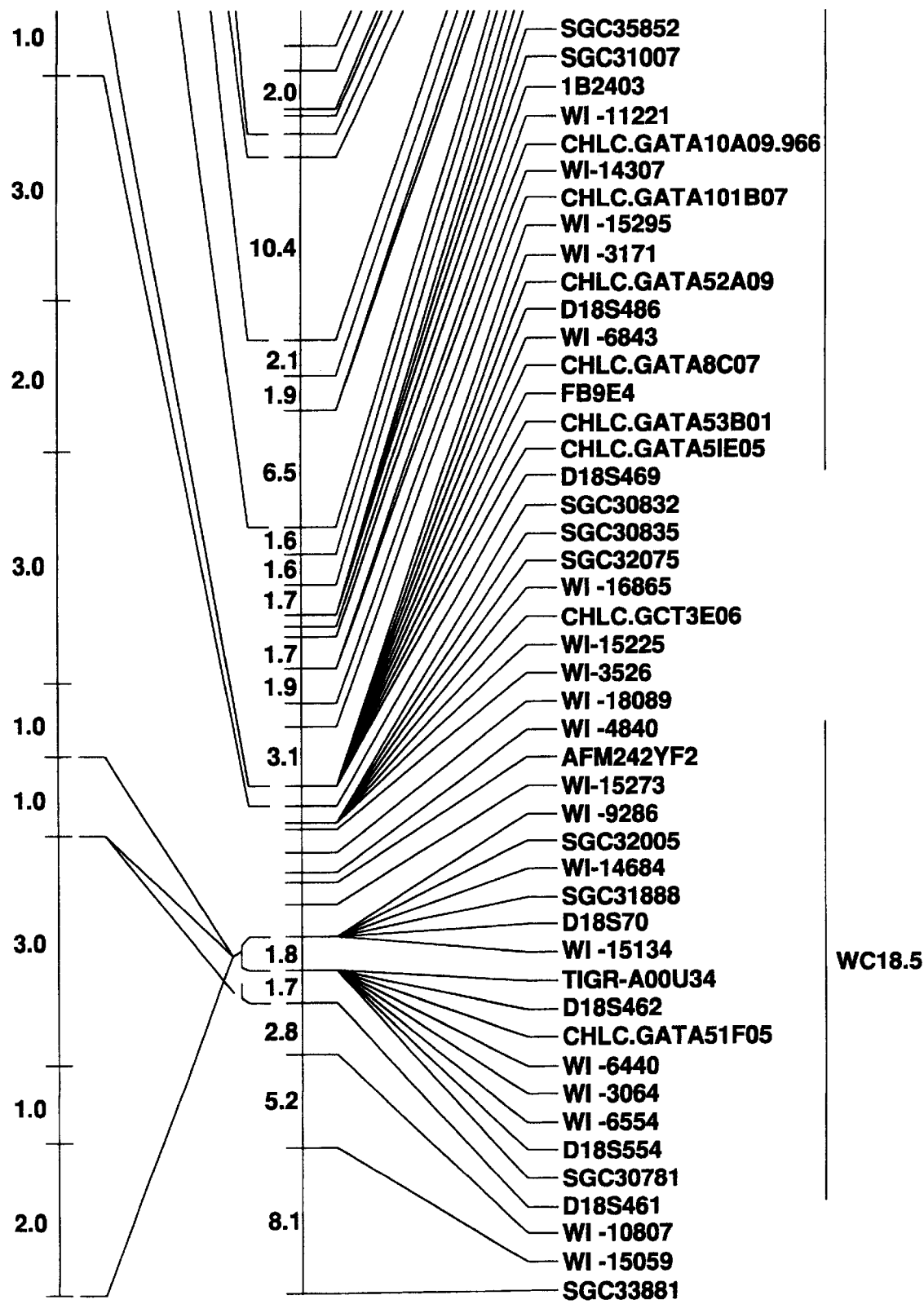

Of the 473 microsatellites analyzed with two-point linkage tests, 23 markers exceeded the empirically determined thresholds designated for the coverage calculations (in either CR001, CR004, or in the combined data set). The location of these markers, the peak lod scores obtained in each family and in the combined data set, and the maximum likelihood estimate of the recombination fraction (0) at which these lod scores were observed are indicated in Table 1. The approximate chromosomal locations of these markers are also depicted in FIGS. 5A and 6B. The distribution of lod scores (for the maximum likelihood estimate of 0 in the combined data set) across the genome is displayed by chromosome in FIG. 2.

Figure 3:
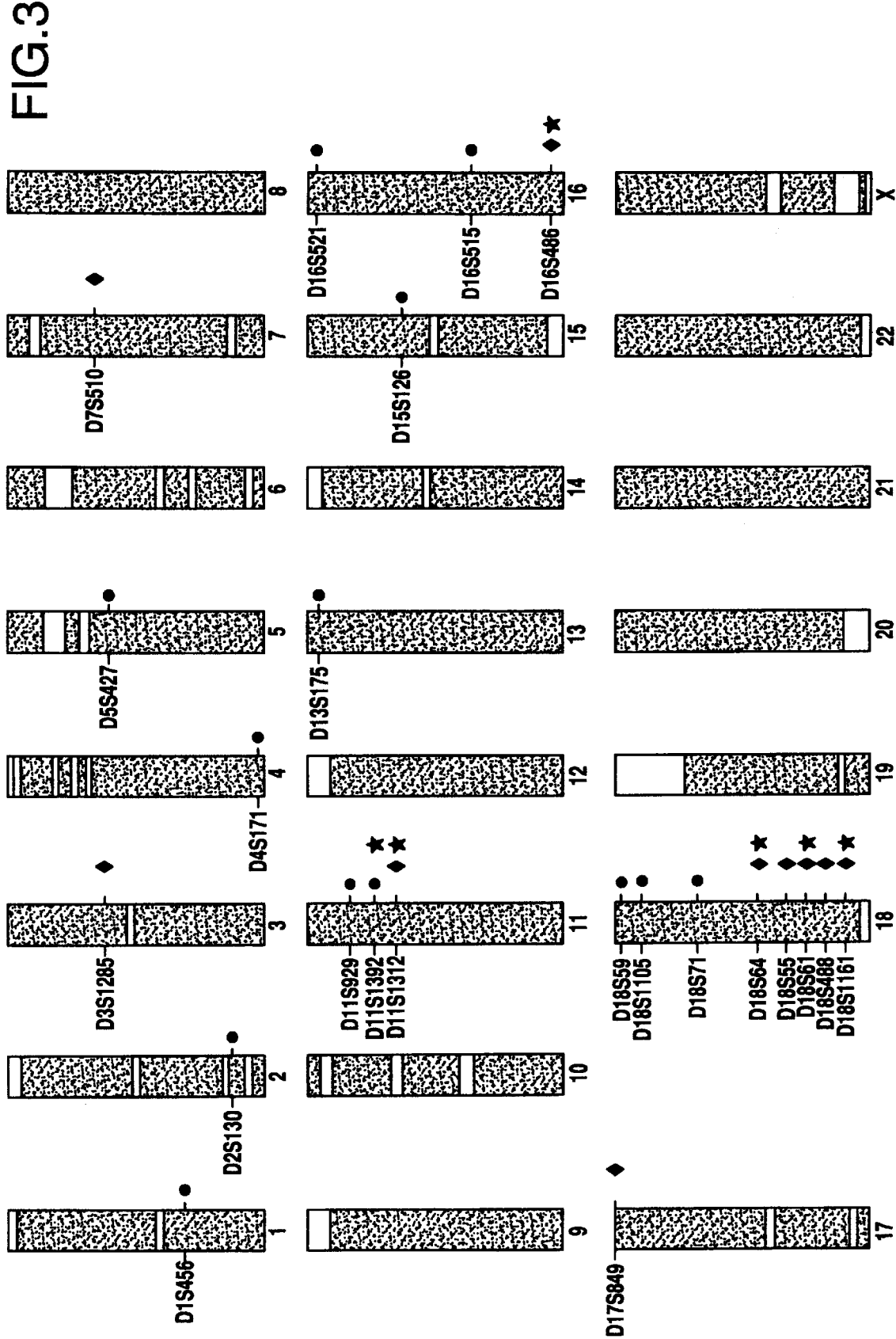
FIG. 3 depicts the extent of marker coverage used in the pedigree genome screening study for each chromosome. Coverage is defined as regions for which a lod score of at least 1.6 would have been detected (in the combined data set) for markers truly linked to BP-I under the model employed. Areas that remain uncovered (at this threshold) are unshaded. Markers for which lod scores were obtained that exceeded the empirically determined coverage thresholds in CR001, CR004, or the combined data set, are shown at their approximate chromosomal location. The symbols to the right of the chromosome indicate the thresholds exceeded at that marker: a circle signifies that the lod score at a marker exceeded the threshold of 0.8 in CR001, a diamond signifies that the lod score exceeded the threshold of 1.2 in CR004, and a star signifies that the lod score exceeded the threshold of 1.6 in the combined data set.
Figure 4A:
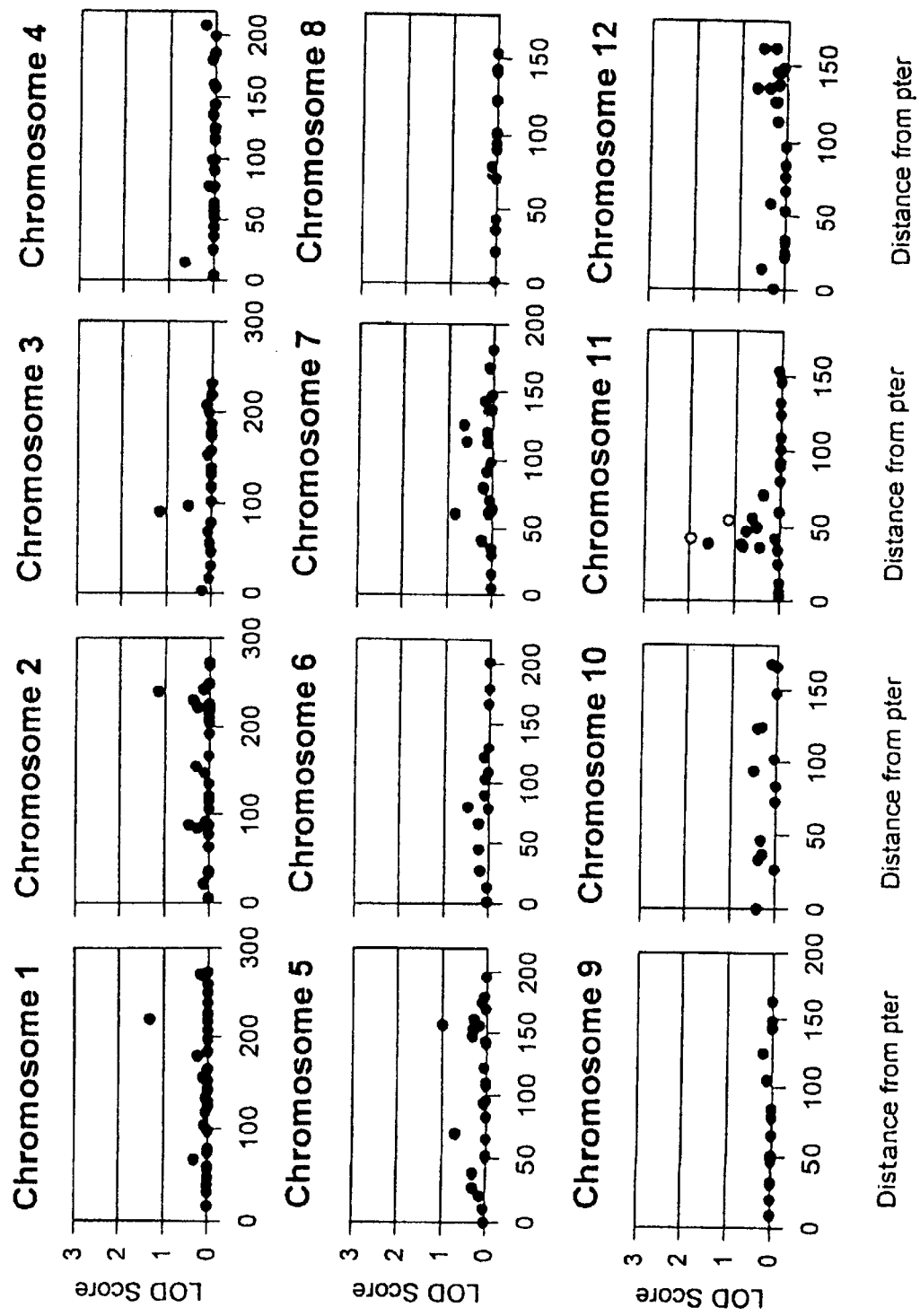
FIGS. 4A and 4B depicts the Lod score for the maximum likelihood estimate of theta in the combined sample for the 473 microsatellite markers typed in the pedigree genome screen. The MLEs of theta are represented by different colors: red=theta<0.10; green=0.10≦theta≦0.40; blue= theta≧0.40. Note that the scale for the x-axis (distance from pter) changes with chromosomes.
Figure 4B:
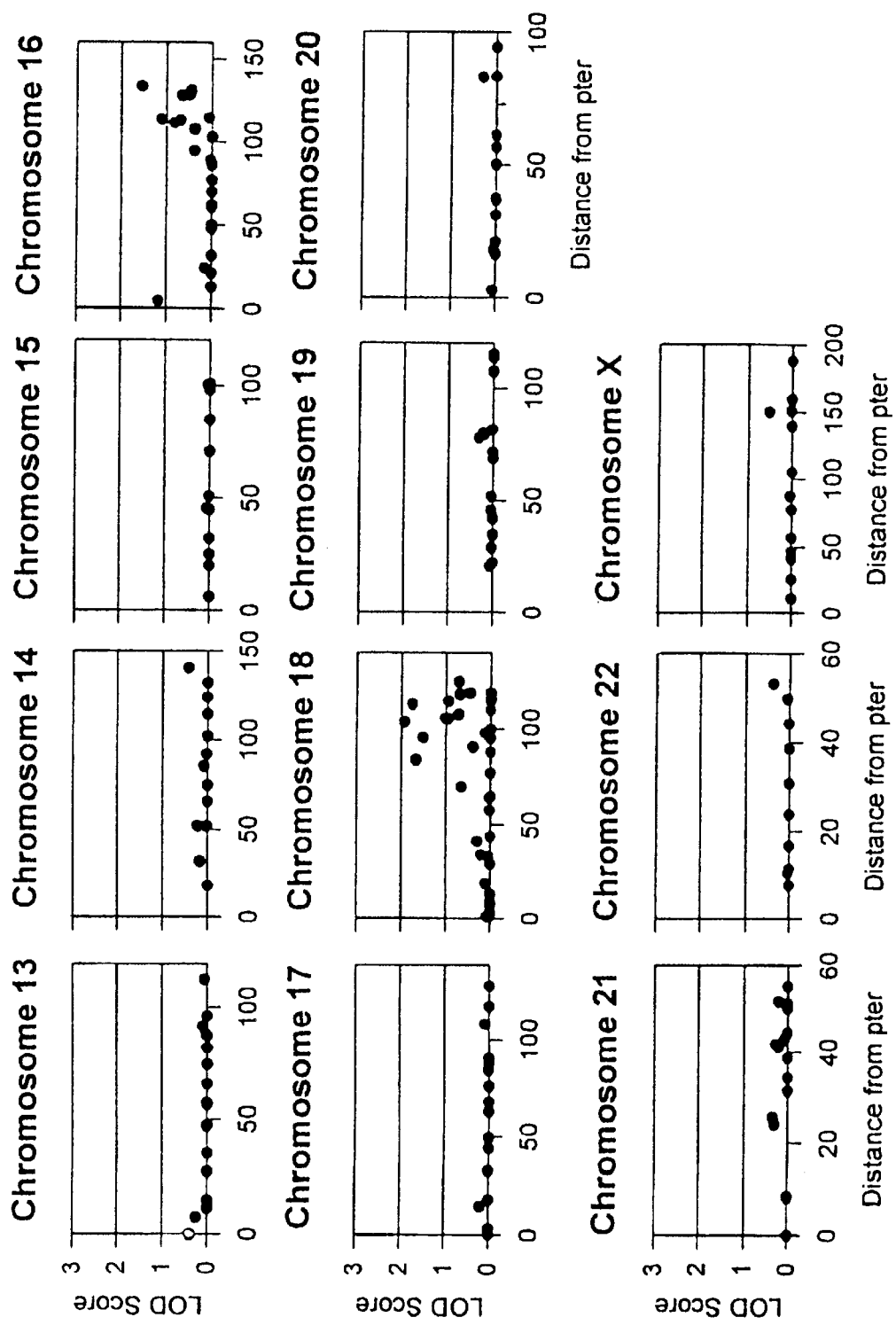

Five markers in the 18q22-q23 region exceeded the lod score thresholds in pedigree CR004. See FIGS. 2 and 3.

UNRELATED BP-I CRCV PATIENT STUDY RESULTS

Out of the forty-two markers tested, eight displayed evidence of over-representation of a particular allele on disease chromosomes. Eight of the 42 markers had −2*ln (likelihood ratio) statistics >1.0. Three other markers had −2*ln(likelihood ratio) statistics >0 and <0.62. The results are shown in Table I:

TABLE I

| Marker | Allele Size | Frequency on non-disease Chromosomes | Frequency on Disease Chromosomes |
|---|---|---|---|
| D18S59 | 154 | 0.121 | 0.572 |
| D18S476 | 271 | 0.470 | 0.771 |
| D18S467 | 172 | 0.384 | 0.693 |
| D18S61 | 177 | 0.074 | 0.326 |
| D18S485 | 182 | 0.237 | 0.586 |
| D18S870 | 179 | 0.405 | 0.657 |
| D18S469 | 234 | 0.128 | 0.450 |
| D18S1121 | 168 | 0.171 | 0.553 |

Five of these eight marker loci were clustered within a small region of 18q22-q23 that overlapped the region of maximal haplotype sharing among affected individuals in CR001 and CR004. The strongest LD in 18q22-q23 was observed at D18S1121 (−2*In(likelihood ration) of 5.03, p=0.01); it is noteworthy that at this locus a specific allele (of 168 bp) is over-represented on the disease chromosomes in the population BP-I sample and is also present on the predominant high-risk haplotype within the pedigrees. Fifteen of 17 affected individuals in CR004, and 4 of 9 affected individuals in CR001 possessed the 168 b.p. allele at D18S1121.

The LD and pedigree findings in the 18q23 region denote a clearly delineated region flanked by markers D18S469 and D18S554 that contains a BP-I susceptibility locus. Results of additional LD analyses using additional markers are suggestive of a potential gene involved in BP-I susceptibility in a region of 18q22-q23 defined by markers D18S1121 and D18S380, inclusive. These regions are distinct from other regions on chromosome 18 that have been suggested as linked to mood disorder phenotypes (more broadly defined than BP-I). See FIGS. 5A, 5B. In contrast to previous reports by Berrettini et al. and Stine et al., suggesting possible linkage between mood disorder and markers in the pericentromeric region of chromosome 18, our results did not show any evidence for association of BP-I with any pericentromeric markers (D18S378, D18S53, D18S453 or D18S40).

ADDITIONAL FINE MAPPING STUDIES

In order to further delineate regions of BP-I susceptibility within the 18q22-q23 region, additional unrelated BP-I patients from the CRCV as well as other populations are diagnosed and genotyped both with the markers described herein as well as additional markers in the 18q23 region that are known as well those yet to be identified. Additional markers are available from the Cooperative Human Linkage Center (CHLC) public database, from newer Genethon and CHLC maps as they become available (Murray, J. C. et al. (1944) Science 265, 2049–2054, Gyapay, G., et al. (1994) Nature Genet. 7,246–339) and from the public database of the Utah Center for Genome Research (all of which are incorporated by reference herein). The web addresses for Genethon and CHLC are: Genethon (http://www.genethon.fr/genethon_en.html), CHLC (http://gopher.chlc.org/HomePage.html). These databases are all linked, and one of ordinary skill in the art can readily access the information available from these databases.

The markers shown in FIG. 6B, can be used to genotype the CRCV pedigrees and unrelated BP-I patients described herein as well as other BP-I affected individuals and pedigrees. See FIG. 6B (portion of a chromosome 18 map available from the Whitehead Institute, web address: http://133.30.8.1:8080/=@=:www-genome.wi.mit.edu. (incorporated herein by reference)). The fine mapping techniques described herein in conjunction with the teachings regarding the 18q23 region can be used to further narrow the BP-I susceptibility region.

IDENTIFICATION OF NEW MARKERS FROM THE 18Q23 REGION

Cloned human genomic DNA covering the target region is assembled. Microsatellite sequences from these clones are identified. A sufficient area around the repeat to enable development of a PCR assay for genomic DNA is sequenced, and it is confirmed that the microsatellite sequence is polymorphic, as several uninformative microsatellites are expected in any set. Several methods have been routinely used to identify microsatellites from cloned DNA, and at this time no single one is clearly preferable (Weber, 1990, Hudson et al., 1992). Most of these require screening an excessive number of small insert clones or performing extensive subcloning using clones with larger inserts.

New strategies have recently been developed which permit the use of the several different microsatellites to be found within a single large insert clone without requiring extensive subcloning. A method for direct identification of microsatellites from yeast artificial chromosomes (YACs) provides several new markers from the target region. This procedure is based on a subtractive hybridization step that permits separation of the target DNA from the vector background. This step is useful because the human DNA (the YAC) constitutes only a small proportion of the total yeast genomic DNA.

YAC clones (with inserts averaging about 750 Kb of human genomic DNA) that span the 18q22-q23 region have already been identified by the CEPH/Généthon consortium (Cohen et al., 1993) and are publicly available. The markers from YACs that have been mapped to portions of the candidate region that are not well represented by currently available markers are first isolated. By typing these markers in the families and the "LD" sample, as described above, it is possible to narrow the candidate region, perhaps to a size of less than one to two cM, thus permitting limitation of the segment in which more extensive mapping efforts are applied.

Briefly, the microsatellite identification procedure is performed as follows: A subtractive hybridization is performed using genomic DNA from a target YAC together with an equivalent amount of a control DNA. This procedure separates the YAC DNA from that of the yeast vector. Following the subtraction procedure the subtracted YAC DNA is purified, digested with restriction enzymes and cloned into a plasmid vector (Ostrander et al., 1992). The cloned products of each YAC are screened using a CA(15) oligonucleotide probe. Each positive clone (i.e. those that contain TG-repeats) is sequenced to identify primers for PCR to genotype the BP-I samples.

An alternative approach, based on using a set of degenerate sequencing primers that anneal directly to the repeat sequence, permitting direct thermal cycle sequencing (Browne & Litt, 1992), can also be used.

Once the candidate region is narrowed to a size of less than about 500 to 1000 Kb, a contiguous array (contig) of clones with smaller inserts than YACs, mainly P1 clones, is developed. P1 clones are phage clones specially designed to accommodate inserts of up to 100 Kb (Shepherd et al., 1994).

DEVELOPMENT OF A PHYSICAL MAP OF THE 18Q22–Q23 REGION

In parallel with the genetic mapping, a physical map of the 18q22-q23 region is developed. The backbone of this effort is the assembly of contigs of large insert clones. Low resolution contigs for most of the human genome are already available using the YACs developed by CEPH (Cohen et al., 1993). Although these have been individually verified and checked for overlap with other YACs, there is a high rate of chimerism in the YACs and insufficient evidence to definitively confirm the order of the YACs. In addition, because of their large size these YACs are particularly cumbersome to work with. Nevertheless, they provide a useful framework to start constructing high resolution contigs.

Once a candidate region of less than about five cM is delineated, the studies to develop a physical map are commenced. Because of the disadvantages of relying solely oa YACs, and because positional cloning is facilitated by the availability of a higher resolution map, contigs are generated using P1 clones once the candidate region is narrowed to less than one Mb, by LD mapping in the expanded population sample using the new markers identified from the YACs.

Once a region of 500–1000 Kb or less is defined, physical mapping and cloning are computed using P1 clones rather than YACS, and P1 contigs over such a region are constructed. The P1s are used to identify additional markers for the further positional cloning steps as well as the screening for rearrangements.

The starting point of contig construction is the microsatellite sequences and non-polymorphic STSs that derive from the few YACs that surround the genetically determined candidate region. These STSs are used to screen the P1 library. The ends of the P1s are cloned using inverse PCR and used to order the P1s relative to each other. Amplification in a new P1 will indicate that it overlaps with the previous one. Fluorescent in situ hybridization (FISH) permits ordering of the majority of the P1s (Pinkel, 1988; Lichter, 1991). The original set of P1s serves as building blocks of the complete contig; each end clone is used to re-screen the library and in this way P1s are added to the map.

From each P1 additional microsatellites are identified as previously described. This allows further reduction of the candidate region. When the region is narrowed to less than one Mb in size, positional cloning efforts are initiated.

USE OF P1 CLONES TO IDENTIFY CANDIDATE cDNAs FOR SCREENING FOR MUTATIONS IN THE DNA OF BP-I PATIENTS

The P1 clones are used to identify candidate cDNAs. The candidate cDNAs are subsequently screened for mutations in DNA from BP-I patients. From the minimal candidate region defined by genetic mapping experiments a segment is left that is sufficiently large to contain multiple different genes.

IDENTIFICATION OF CODING SEQUENCES

Coding sequences from the surrounding DNA are identified, and these sequences are screened until a probable candidate cDNA is found. Much of the human genome will be sequenced over the next few years, in which case it may become feasible to identify coding sequences through database screening. Candidates may also be identified by scanning databases consisting of partially sequenced cDNAs (Adams et al., 1991), known as expressed sequence tags, or ESTs. These resources are already largely developed, and include upwards of 100,000 cDNAs, the majority expressed primarily in the brain. It is not yet clear, however, that the complete set of cDNAs will be mapped to specific chromosomal locations in the near future, and that their data will soon be made publicly available. The database can be used to identify all cDNAs that map to the minimal candidate region for BP-I. These cDNAs are then used as probes to hybridize to the P1 contig, and new microsatellites are isolated, which are used to genotype the "LD" sample. Maximal linkage disequilibrium in the vicinity of one or two cDNAs is identified. These cDNAs are the first ones used to screen patient DNA for mutations. Database screening has already been used to identify a gene responsible for familial colon cancer (Papadopolous et al., 1993).

Coding sequences are also identified by exon amplification (Duyk et al., 1990; Buckler et al., 1991). Exon amplification targets exons in genomic DNA by identifying the consensus splice sequences that flank exon-intron boundaries. Briefly, exons are trapped in the process of cloning genomic DNA (e.g. from P1s) into an expression vector (Zhang et al., 1994). These clones are transfected into COS cells, RT-PCR is performed on total or cytoplasmic RNA isolated from the COS cells using primers that are complementary to the splicing vector. Exon amplification is tedious but routine; for example, the system developed by Buckler et al. (1991). This method is probably preferable to another widely used approach, direct selection, which involves screening cDNAs using large insert clone contigs, with several steps to maximize the efficiency of hybridization and recovery of the appropriate hybrid (Lovett et al., 1991). Although direct selection is more efficient than exon amplification (Del Mastro et al., 1994), it may not be practical as it depends on the candidate cDNA being expressed in the tissue from which the cDNA library was made; there is no prior information to indicate the tissue or developmental stage in which BP-I genes would be expressed.

Once cDNAs are identified the most plausible candidates are screened by direct sequencing, SSCP or using chemical cleavage assays (Cotton et al. 1988).

The data are also evaluated for clues to the possible identity or mode of action of BP-I mutations. For example, it is known that trinucleotide repeat expansion is associated with the phenomenon of anticipation, or the tendency for a phenotype to become more severe and display an earlier age of onset in the lower generations of a pedigree (Ballabio, 1993). Several investigators have suggested that segregation patterns of BP-I are consistent with anticipation (McInnis et al., 1993; Nylander et al., 1994). The apparent transmission of BP-I, in association with the conserved 18q23 haplotype is constant with anticipation. Therefore, once the candidate region is narrowed to its minimal extent, the P1 clones are screened using trinucleotide repeat oligonucleotides (Hummerich et al., 1994). A PCR assay is developed and patient DNAs are screened for expanded alleles.

Genetic and physical data help to map the bipolar mood disorder gene to the 18q22-q23 region of chromosome 18. New markers from this region are tested in order to locate the bipolar mood disorder gene in a region small enough to provide higher quality genetic tests for bipolar mood disorder, and to specifically find the mutated gene. Narrowing down the region in which the gene is located will lead to sequencing of the bipolar mood disorder gene as well as cloning thereof. Further genetic analysis employing, for example, new polymorphisms flanking D18S59 and D18S476 as well as the use of cosmids, yeast artificial chromosome (YAC) clones, or mixtures thereof, are employed in the narrowing down process. The next step in narrowing down the candidate region includes cloning of the chromosomal region of 18q22-q23 including proximal and distal markers in a contig formed by overlapping cosmids and YACS. Subsequent subcloning in cosmids, plasmids or phages will generate additional probes for more detailed mapping.

The next step of cloning the gene involves exon trapping, screening of cDNA libraries, Northern blots or rt PCR (reverse transcriptase PCR) of samples from affected and unaffected individuals, direct sequencing of exons or testing exons by SSCP (single strand conformation polymorphism), RNase protection or chemical cleavage.

Flanking markers on both sides of the bipolar mood disorder gene combined with D18S59 and D18S476 or a number of well-positioned markers that cover the chromosomal region (18q22-q23) carrying the disease gene, can give a high probability of affected or non-affected chromosomes in the range of 80–90% accuracy, depending on the informativeness of the markers used and their distance from the disease gene. Using current markers linked to bipolar mood disorder, and assuming closer flanking markers will be identified, a genetic test for families with bipolar mood disorder will be for diagnosis in conjunction with clinical evaluation, screening of risk and carrier testing in healthy siblings. In the future, subsequent delineation of closely linked markers which may show strong disequilibrium with the disorder, or identification of the defective gene, could allow screening of the entire at-risk population to identify carriers, and provide improved treatments.

TREATMENT OF BP-I PATIENTS USING GENOTYPE DATA

Using the fine mapping techniques described herein, BP-I susceptibility loci or genes in the 18q22-q23 region are identified and used to genotype patients diagnosed phenotypically with BP-I. Genotyping with the markers described herein as well as additional markers permits confirmation of phenotypic BP-I diagnoses or assist with ambiguous clinical phenotypes which make it difficult to distinguish between BP-I and other possible psychiatric illnesses. A patient's genotype in the 18q22-q23 region is determined and compared with previously determined genotypes of other individuals previously diagnosed with BP-I. Once an individual is genotyped as having a BP-I susceptibility locus in the 18q22-q23 region, the individual is treated with any of the known methods effective in treating at least certain individuals affected with BP-I. These known methods include the administration of drugs including antidepressants such as lithium salts, carbamazepine, valproic acid, lysergic acid diethylamide (LSD), p-chlorophenylalanine, p-propyldopacetamide dithiocarbamate derivatives such as FLA 63; anti-anxiety drugs, including diazepam, monoamine oxidase (MAO) inhibitors including iproniazid, cloryline, phenelzine and isocarboxazid; biogenic amine uptake blockers, e.g., tricyclic antidepressants such as desipramine, imipramine and amitriptyline; serotonin reuptake inhibitors, e.g., fluoxetine; antipsychotic drugs such as phenothiazaine derivatives (e.g., chlorpromazine (thorazine), and trifluopromazine, butyrophenones (e.g., haloperidol (Haldol), thioxanthine derivatives (e.g., chlorprothixene); and dibenzodiazpines (e.g., chlozapine); benzodiazpines; dopaminergic agonist and antagonists, e.g., L-Dopa, cocaine, amphetamine, α-methyl-tyrosine, reserpine, tetrabenazine, benzotropine, pargyline; noradrenergic agonists and antagonists, e.g., clonidine, phenoxybenzamine, phentolamine, and tropolone. Many of these drugs are used in combination.

Studies are conducted correlating effective treatments with BP-I genotypes in the 18q22-q23 region to determine the most effective treatments for particular genotypes. BP-I patients can then be genotyped in the 18q22-q23 region and the statistically most effective treatment can be determined as a first course of therapy.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of predicting a patient's likelihood of developing bipolar mood disorder comprising:
   determining a patient's genotype in a region on the long arm of chromosome 18, said determining comprising determining an allele size in a DNA sample derived from a patient at a marker located between markers D18S469 and D18S554, inclusive; and
   comparing said patient's genotype to a genotype of an affected individual, wherein a sharing of an allele size at a marker located between D18S469 and D18S554, inclusive, between the patient and affected individuals is an indication of an increased likelihood that the patient will develop bipolar mood disorder.

2. The method of claim 1, wherein said patient's genotype is determined in a region on the long arm of chromosome 18 between markers D18S1121 and D18S380, inclusive.

3. The method of claim 1, wherein said patient's genotype is determined in a region on the long arm of chromosome 18 between markers D18S 1121 and D18S469, inclusive.

4. A method of claim 1, wherein said patient has Spanish or Amerindian ancestry.

5. A method of predicting a patient's likelihood to respond to drug treatment for bipolar mood disorder (BP) comprising:
   determining a patient's genotype in a region on the long arm of chromosome 18, wherein said determining comprises determining an allele size in a DNA sample derived from said patient at a marker located between markers D18S469 and D18S554, inclusive; and
   comparing said patient's genotype to a genotype of an affected individual, wherein a sharing of an allele size at a marker located between markers D18S469 and D18S554, inclusive, is an indication of an increased likelihood that a drug treatment for BP will be effective.

6. A method of detecting the presence of a bipolar mood disorder susceptibility locus in an individual comprising:
   analyzing a sample of DNA from said individual for the presence of a DNA polymorphism on the long arm of chromosome 18 between D18S469 and D18S554, inclusive, wherein said DNA polymorphism is associated with bipolar mood disorder.

7. The method of claim 6, wherein said DNA polymorphism is located on the long arm of chromosome 18 between D18S469 and D18S1161, inclusive.

8. The method of claim 6, wherein said DNA polymorphism is located on the long arm of chromosome 18 between D18S1161 and D18S1121, inclusive.

9. The method of claim 6, wherein said DNA polymorphism is located on the long arm of chromosome 18 between D18S1121 and D18S1009, inclusive.

10. The method of claim 6, wherein said DNA polymorphism is located on the long arm of chromosome 18 between D18S1109 and D18S380, inclusive.

11. The method of claim 6, wherein said DNA polymorphism is located on the long arm of chromosome 18 between and D18S380 and D18S554, inclusive.

12. The method of claim 6, wherein said DNA polymorphism is located on the long arm of chromosome 18 between D18S1009 and D18S554, inclusive.

13. The method of claim 6, wherein said analyzing further comprises:
   a. obtaining DNA samples from family members of said individual,
   b. analyzing said DNA samples from family members for the presence of said DNA polymorphism, and
   c. correlating the presence or absence of the DNA polymorphism with a phenotypic diagnosis of bipolar mood disorder for said individual and for said family members wherein the correlation is indicative of a bipolar mood disorder susceptibility locus.

14. A method for detecting the presence of a bipolar mood disorder susceptibility DNA polymorphism in an individual comprising:
   a) typing blood relatives of said individual for a DNA polymorphism located within a region of chromosome 18, wherein said region is located between D18S469 and D18S554, inclusive; and
   b) analyzing a DNA sample from said individual for the presence of said DNA polymorphism, wherein the presence of said DNA polymorphism in said region in an individual is indicative of an increased likelihood that the individual will develop bipolar mood disorder.

15. A method of genetically diagnosing bipolar mood disorder in an individual comprising:
   analyzing a DNA sample from an individual for the presence of a DNA polymorphism associated with bipolar mood disorder, wherein said DNA polymorphism is located within a region of chromosome 18, wherein said region is located between D18S1121 and D18S554, inclusive, wherein the presence of said DNA polymorphism is an indication that the individual has bipolar mood disorder.

16. A method of confirming a phenotypic diagnosis of bipolar mood disorder in an individual comprising:
   analyzing a DNA sample from an individual for the presence of a DNA polymorphism associated with bipolar mood disorder, wherein said DNA polymorphism is located within a region of chromosome 18, wherein said region is located between D18S1121 and D18S554, inclusive, wherein the presence of said DNA polymorphism confirms a phenotypic diagnosis of bipolar mood disorder.

17. The method of claim 16, wherein said individual has Spanish or Amerindian ancestry.

18. A method of treating an individual phenotypically diagnosed with bipolar mood disorder comprising:
   a) analyzing a DNA sample from an individual phenotypically diagnosed with bipolar mood disorder for the presence or absence of a DNA polymorphism associated with bipolar mood disorder, wherein said DNA polymorphism is located within a region of chromosome 18, wherein said region is located between D18S469 and D18S554, wherein the presence of a DNA polymorphism associated with BP confirms the phenotypic diagnosis of BP; and
   b) selecting a treatment plan that is most effective for individuals phenotypically diagnosed as having BP.

* * * * *

UNITED STATES PATENT AND TRADEMARK OFFICE
CERTIFICATE OF CORRECTION

PATENT NO. : 6,136,532
DATED : October 24, 2000
INVENTOR(S) : Freimer et al.

Page 1 of 1

It is certified that error appears in the above-identified patent and that said Letters Patent is hereby corrected as shown below:

Please add the name --Susan Service-- to the 'Inventors Section' on the first page of the printed patent.

Signed and Sealed this

Tenth Day of July, 2001

Attest:

*Attesting Officer*

NICHOLAS P. GODICI
*Acting Director of the United States Patent and Trademark Office*